United States Patent [19]

Tavecchia et al.

US005599791A

[11] Patent Number: 5,599,791
[45] Date of Patent: Feb. 4, 1997

[54] AMIDES OF ANTIBIOTIC GE 2270 FACTORS

[75] Inventors: Paolo Tavecchia, Rho; Sergio Lociuro, Milan; Romeo Ciabatti, Novate Milanese; Enrico Selva, Gropello Cairoli, all of Italy

[73] Assignee: Gruppo Lepetit SPA, Varese, Italy

[21] Appl. No.: 84,189

[22] PCT Filed: Jan. 2, 1992

[86] PCT No.: PCT/EP92/00002

§ 371 Date: Jul. 1, 1993

§ 102(e) Date: Jul. 1, 1993

[87] PCT Pub. No.: WO92/12172

PCT Pub. Date: Jul. 23, 1992

[30] Foreign Application Priority Data

Jan. 3, 1991 [EP] European Pat. Off. ............... 91100123

[51] Int. Cl.[6] .................... C07K 7/56; A61K 35/66

[52] U.S. Cl. .................................. 514/9; 540/451
[58] Field of Search .................... 540/451; 514/9

[56] References Cited

U.S. PATENT DOCUMENTS 5,139,778 8/1992 Selva ........................................ 424/117

OTHER PUBLICATIONS

Selva II The Journal of Antibiotics,44(7)693) (1991).
Lancaster Catalog pp. 589, 590, 1991 Windhan, N.H.

Primary Examiner—Robert Gerstl
Attorney, Agent, or Firm—J. Michael Dixon

[57] ABSTRACT

The present invention is directed to novel amide derivatives of antibiotic GE 2270 compounds and a process for preparing them. Said amide derivatives are antimicrobial agents active against gram positive bacteria as well as gram negative bacteria.

13 Claims, No Drawings

AMIDES OF ANTIBIOTIC GE 2270 FACTORS

The present invention is directed to novel amide derivatives of antibiotic GE 2270 having the following formula I

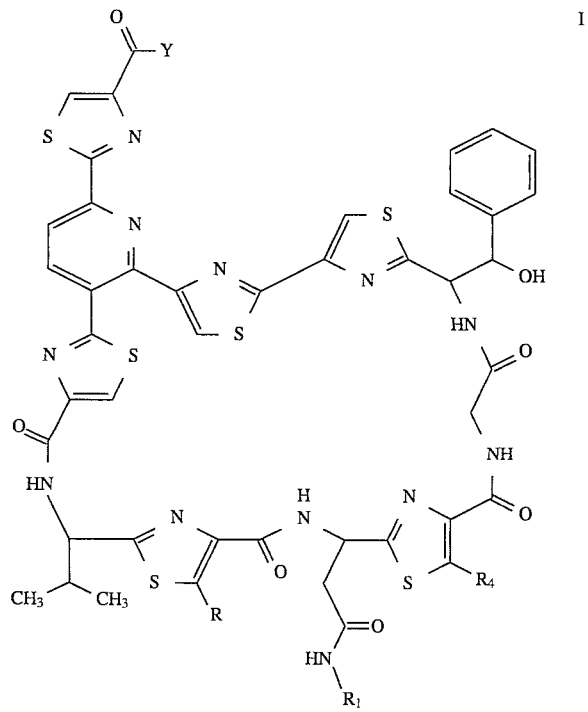

wherein
- R represents:
  hydrogen, hydroxymethyl, or methoxymethyl;
- $R_1$ represents:
  hydrogen, or methyl:
- Y represents:
  a group of formula

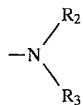

wherein:
- $R_2$ represents:
  hydrogen, $(C_1-C_4)$alkyl, amino$(C_2-C_4)$alkyl, $(C_1-C_4)$alkylamino-$(C_1-C_4)$alkyl, or di-$(C_1-C_4)$alkylamino-$(C_1-C_4)$alkyl;
- $R_3$ represents:
  hydrogen, a linear or branched $(C_1-C_{14})$alkyl group bearing from 1 to 3 substituents selected from: carboxy, sulfo, phosphono, amino which may be optionally protected with a lower alkoxycarbonyl or a benzyloxycarbonyl group, $(C_1-C_4)$alkylamino wherein the alkyl moiety may be optionally substituted with a carboxy group, di-$(C_1-C_4)$alkylamino, hydroxy, halo, $(C_1-C_4)$alkoxy wherein the alkyl moiety may be optionally substituted with a carboxy group, $(C_1-C_4)$alkoxycarbonyl, mercapto, $(C_1-C_4)$alkylthio wherein the alkyl moiety may be optionally substituted with a carboxy group, phenyl which may be optionally substituted with 1 to 3 substituents selected from carboxy, sulfo, hydroxy, halo and mercapto, carbamyl, $(C_1-C_6)$alkylcarbamyl wherein the alkyl moiety may be optionally substituted with 1 or 2 substituents selected from carboxy, amino, $(C_1-C_4)$alkylamino and di-$(C_1-C_4)$alkylamino, di-$(C_1-C_4)$alkylcarbamyl wherein the alkyl moieties together with the adjacent nitrogen atom may also represent a saturated 5–7 membered heterocyclic ring which may optionally be substituted with a carboxy or a carbamyl group on one of the ring carbons and may optionally contain a further heterogroup selected from O, S and N, benzoylamino wherein the phenyl group may be substituted from 1 to 3 hydroxy group, a nitrogen containing 5–6 membered heterocyclic ring which may be unsaturated, partially saturated or wholly saturated and may contain 1 to 3 further heteroatoms selected from N, S and O wherein one of the carbons of the ring may optionally bear a group carboxy, sulfo, carboxy$(C_1-C_4)$alkyl and sulfo$(C_1-C_4)$alkyl and the ring nitrogen atom may optionally be substituted by $(C_1-C_4)$alkyl, carboxy$(C_1-C_4)$alkyl, sulfo$(C_1-C_4)$alkyl, and benzyl;
- $(C_3-C_6)$alkenyl, optionally substituted by carboxy or sulfo;
- 1-deoxy-1-glucityl;
- 2-deoxy-2-glucosyl;
- a fully saturated 5 to 7 membered nitrogen containing heterocyclic ring wherein the nitrogen atom may be optionally substituted by $(C_1-C_4)$alkyl or benzyl and one or two carbons of the ring skeleton may bear a substituent selected from $(C_1-C_4)$alkyl, carboxy and sulfo;

or $R_2$ and $R_3$ taken together with the adjacent nitrogen atom represent a fully saturated 5–7 membered heterocyclic ring which may optionally contain a further heteroatom selected from O, S and N, and may optionally bear one or two substituents on the ring carbons selected from $(C_1-C_4)$alkyl, benzyl, carboxy, sulfo, carboxy$(C_1-C_4)$alkyl, and sulfo$(C_1-C_4)$alkyl;

$R_4$ represents
  hydrogen, methyl, or hydroxymethyl
with the proviso that when $R_4$ is hydrogen or hydroxymethyl, then simultaneously R is methoxymethyl and $R_1$ is methyl;
and the pharmaceutically addition salts thereof.

This invention includes also a process for preparing the compounds of this invention from the corresponding starting compounds of formula (II)

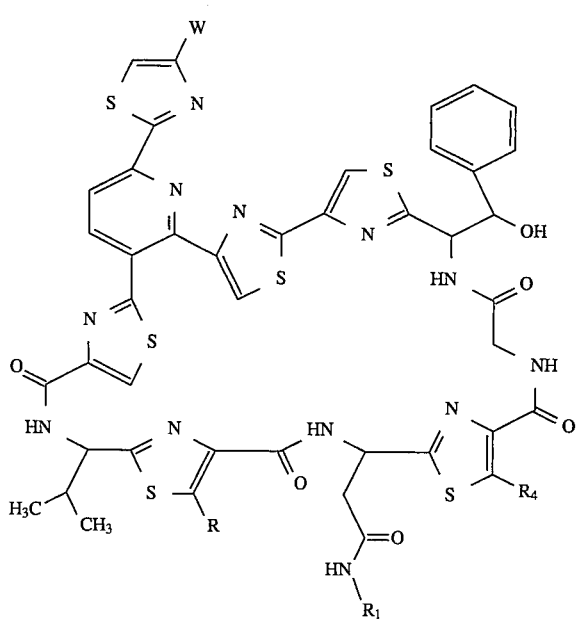

II wherein W is a carboxylic function or an activated ester thereof.

Antibiotic GE 2270 is prepared by culturing a sample of *Planobispora rosea* ATCC 53773 or a producing variant or mutant thereof and isolating the desired antibiotic substance from the mycelium and/or the fermentation broth. *Planobispora rosea* ATCC 53773 was isolated from a soil sample and deposited on Jun. 14, 1988 with the American Type Culture Collection (ATCC), 12301 Parklawn Drive, Rockville, Md. 20852 Maryland, U.S.A., under the provisions of the Budapest Treaty.

The strain has been accorded accession number ATCC 53773.

Antibiotic GE 2270 factor A is the main component of the antibiotic GE 2270 complex.

Antibiotic GE 2270 factor A and *Planobispora rosea* ATCC 53773 are described in European Patent Application Publication No. 359062.

Recent studies showed that antibiotic GE 2270 factor A can be represented by the following general formula III

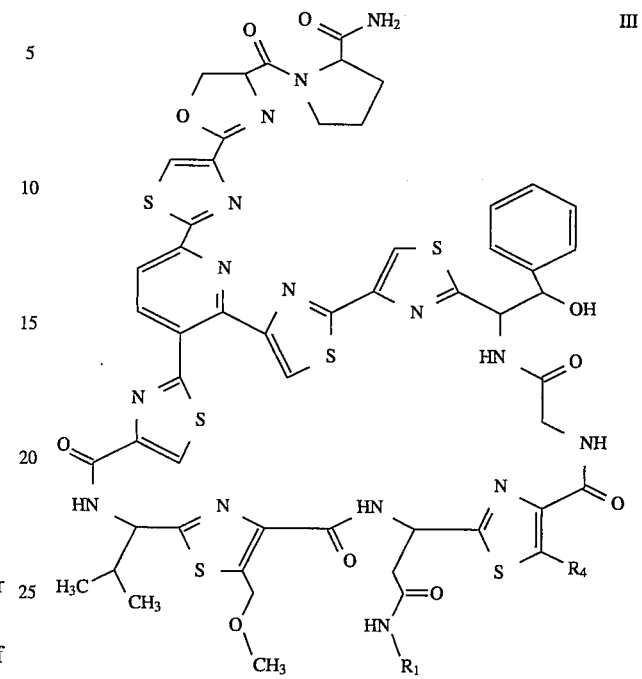

III

When antibiotic GE 2270 factor A is treated under selective hydrolysis conditions some derivatives named antibiotic GE 2270 factor $A_1$, $A_2$ and $A_3$ are obtained. Said factors $A_1$, $A_2$ and $A_3$ and the hydrolysis process for preparing then is disclosed in the European Patent Application Publication No. 406745 and U.S. patent application Ser. No. 547,647, U.S. Pat. No. 5,139,778 which is hereby incorporated by reference.

Generally, the above mentioned hydrolytic conditions involve the use of mixtures of buffered or unbuffered aqueous acid media and polar organic solvents. The reaction temperature varies depending on factors such as the strength and the concentration of the acid employed, and is generally comprised between −10° C. and 90° C. Also the reaction time varies considerably depending on parameters such as the temperature, the acid strength and its concentration generally, it may vary from a few minutes to several hours.

In general, when milder hydrolysis conditions are employed, e.g. shorter reaction time and lower temperature or lower acid strength or concentration, antibiotic GE 2270 factor $A_1$ is normally obtained, while stronger hydrolysis conditions yield antibiotic GE 2270 factor $A_2$. To obtain antibiotic GE 2270 factor $A_3$, still more drastic hydrolysis conditions are necessary.

While antibiotic GE 2270 factors $A_2$ and $A_3$ can be directly utilized as the starting materials for the production of the compounds of this invention, antibiotic GE 2270 factor $A_1$ is not suitable as the starting material for direct production of the compounds of this invention; however, it can be utilized as a precursor of the said starting materials as it will be explained further.

Antibiotic GE 2270 factors $A_2$ and factor $A_3$ are characterized by having an ester and a carboxy function respectively in the upper part of the molecule. In particular, it has been found that antibiotic GE 2270 factor $A_2$ and factor $A_3$ can be represented by the above defined formula II wherein:

W represents COOH (antibiotic GE 2270 factor $A_3$) or the ester moiety (antibiotic GE 2270 factor $A_2$)

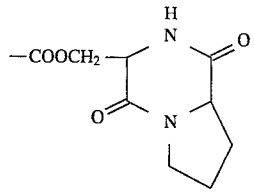

R is methoxymethyl, $R_1$ is methyl and $R_4$ is methyl.

Both antibiotic GE 2270 factor $A_2$ and factor $A_3$ (and mixture thereof) can be used as suitable starting materials for the production of the compounds of the invention, even if factor $A_3$ is the preferred one. Factor $A_2$ may be employed directly as an activated ester or may be converted to factor $A_3$ by drastic acid hydrolysis conditions, as mentioned above, or by basic hydrolysis with diluted alkali (as described in European Patent Application Publication No. 406745 and U.S. patent application Ser. No. 547,647).

It was recently found (European Patent Application Publication No.451486 and U.S. patent application Ser. No. 665,612) which is hereby incorporated by reference that other minor components can be isolated from the cultures of *Planobispora rosea* ATCC 53773 or an antibiotic GE 2270 producing variant or mutant thereof. In particular, they are found in the mycelium and also in the fermentation broths of the cultured microorganism.

A preferred procedure for recovering said minor components of antibiotic GE 2270 from the mycelium includes extracting the filtered or centrifuged mycelium with a water-miscible organic solvent, concentrating the extracts and recovering the crude antibiotic substance by precipitation, optionally with the addition of a precipitating agent, by extraction of the aqueous residue with a water-immiscible organic solvent or by adsorption chromatography followed by elution of the desired product from the absorption matrix.

It was recently found (European Patent Application No. 91114667.8), which correspond to U.S. patent application Ser. No. 07/931,084, filed Aug. 17, 1992 which is hereby incorporated by reference that a further minor component (factor $C_{2a}$) can be isolated from the same culture of *Planobispora rosea* ATCC 53773 described above.

The physico-chemical characteristics of antibiotic GE 2270 $C_{2a}$ are the following:

A) The ultraviolet absorption spectrum recorded with a Perkin Elmer Model 320 spectrometer exhibit the following absorption maxima:

| Solvent | UV max (nm) |
|---|---|
| 0.1M HCl | 245–250 (shoulder) |
| | 300–315 |
| 0.1M KOH | 245–250 (shoulder) |
| | 300–315 |
| Phosphate buffer pH 7.38 | 245–250 (shoulder) |
| | 300–315 |
| Methanol | 245–250 (shoulder) |
| | 300–315 |

B) The $^1$H-NMR spectrum of antibiotic GE 2270 factor $C_{2a}$ was recorded at 250 MHz with a Bruker spectrometer. The spectrum of the antibiotic DNSO-$d_6$ (hexadeuterodimethylsulfoxide) using TMS as the internal standard (0.00 ppm) exhibits following groups of signals [δ, ppm, m] (s=singlet, d=doublet, t=triplet, m=multiplet, Py=pyridine, Tz=thiazole)

9.03, d, (NH); 8.70, d, (2NH's); 8.60, s, 8.54, s, 8.29, s, and 7.38, s, (Tz CH's): 8.48, m, (glycine NH); 8.43, d, and, 8.27, d, (Py CH's); 7.35–7.20, m, (aromatic CH's and primary amide NH); 6.98, s (primary amide NH); 6.04, d, (OH); 5.80, t (OH); 5.35–5.15, m, (αCH's); 5.04, m, (phenylserine βCH); 4.98, s [CH$_2$(OCH$_3$)]; 4.87, d, [CH$_2$(OH)]; 4.81, m and 4.56, m, (oxazoline CH$_2$); 4.35–3.75, m, (CH$_2$ of glycine and prolineamide CH's); 3.39,s, (OCH$_3$); 2.71, m, and 1.30, m, (CH$_2$ of asparagine); 2.48, d, (NCH$_3$ of N-methylasparagine); 2.22–1.80, m, (isopropyl CH and prolineamide CH's); 0.88 and 0.84, d, (valine CH$_3$'s)

C) Antibiotic GE 2270 factor $C_{2a}$ shows retention time ($R_t$) of 12.6 min and retention time relative to antibiotic GE 2270 factor A ($R_t$ 16.6 min) of 0.76 when analyzed with the following reverse phase HPLC system:

Column: Bakerbond® C8 (5 µm) 4.6×250 mm (Bakerbond® is a trade name for reverse phase octylsilyl silica gel HPLC columns supplied by J. T. Baker Research Product, Phillisburg, N.J. 08865 USA)

Flow rate: 1.8 ml/min

Phase A: CH$_3$CN:tetrahydrofuran:40 mM HCOONH$_4$ 40:40:20

Phase B: CH$_3$CN:tetrahydrofuran:40 mM HCOONH$_4$ 10:10:80

Elution: linear gradient from 20% to 30% of Phase A in 20 min

Detection: UV 254 nm

D) The main FAB-MS peak of antibiotic GE 2270 factor $C_{2a}$ is 1306 daltons. This corresponds most likely to the lowest isotope of the protonated molecular ion. The analysis was performed on a Kratos MS-50 double focusing mass spectrometer, using 8 kV accelerating voltage and a saddle field atom gun with Xe gas (2×10$^{-5}$ torr pressure indicated on the source ion gauge) at 6 kV voltage and 1 mA current. The antibiotic for the FAB-MS analysis was mixed with a thioglycerol matrix containing 0.1M acetic acid.

Some of said minor components of antibiotic GE 2270 (i.e. factors $B_1$, $B_2$, $C_1$, $C_2$, $C_{2a}$, $D_1D_2$ and E) may be represented by the general formula II mentioned above wherein W represents the moiety:

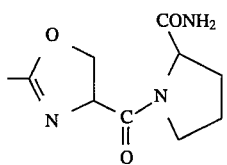

R represents respectively hydrogen for GE 2270 factors $C_1$ and $D_1$ methyl for factor $B_2$, hydroxymethyl for factors $D_2$ and E and methoxymethyl for factors $B_1$, $C_2$ and $C_{2a}$;

$R_1$ represents hydrogen for GE 2270 factors $B_1$, $D_1$ and E and methyl for GE 2270 factors $B_2$, $C_1$, $C_{2a}$ and $D_2$; and $R_4$ represents hydrogen for GE 2270 factor $C_2$, methyl for GE 2270 factors $B_1$, $B_2$, $C_1$, $D_1$, $D_2$ and E and hydroxymethyl for factor $C_{2a}$.

When antibiotic GE 2270 factors $D_1$, $D_2$ and E or mixture thereof are treated by the same hydrolytic process outlined above (and described in European Patent Application Publication No. 406745 and U.S. patent application Ser. No. 547,647) for preparing antibiotic GE 2270 factors $A_2$ and $A_3$ from antibiotic GE 2270 factor A, the common moiety W cited above is hydrolyzed to a carboxy moiety leaving the substituents R, $R_1$ and $R_4$ unaltered.

Therefore, the derivatives of formula II wherein W is a carboxy or an activated ester function, R is hydrogen, hydroxymethyl or methoxyethyl, $R_1$ is hydrogen or methyl and $R_4$ is hydrogen, methyl or hydroxymethyl, with the proviso that when $R_4$ is hydrogen or hydroxymethyl then R is methoxymethyl and $R_1$ is methyl, can be used as starting material of the present invention. It has to be clear that as with other microorganisms, the characteristics of the GE 2270 producing strains are subject to variation. For example, artificial variants and mutants of the strain can be obtained by treatment with various known mutagens, such as U.V. rays, X-rays, high frequency waves, radioactive rays, and chemicals such as nitrous acid, N-methyl-N'-nitro-N-nitroso-guanidine, and many others. All natural and artificial variants and mutants which belong to a species of the genus Planobispora and produce antibiotic GE 2270 are deemed equivalent to strain Planobispora rosea ATCC 53773 for the purposes of this invention.

As used herein, the term "alkyl", either alone or in combination with other substituents, includes both straight and branched hydrocarbons groups; more particularly, "$(C_1-C_{14})$alkyl" represents a straight or branched aliphatic hydrocarbon chain of 1 to 14 carbon atoms such as methyl, ethyl, propyl, 1-methylethyl, butyl, 1-methylpropyl, 1,1-dimethylethyl, pentyl, 1-methylbutyl, 2-methylbutyl, 1-hexyl, 2-hexyl, 3-hexyl, 3,3-dimethyl-1-butyl, 4-methyl-1-pentyl and 3-methyl1-pentyl, heptyl, octyl, nonyl, decyl, undecyl, dodecyl, tridecyl and tetradecyl; likewise, "$(C_1-C_4)$alkyl" represents a straight or branched hydrocarbon chain of 1 to 4 carbon atoms such as those alkyl of 1 to 4 carbons exemplified above.

As described above the "$(C_1-C_{14})$alkyl" moiety may bear 1 to 3 substituents.

The term "halo" represents a halogen atom radical selected from fluoro, chloro, bromo and iodo.

As used herein, the term "$(C_3-C_6)$alkenyl" means an alkylene radical having three to six carbon atoms and a double bond; it comprises propenyl, 3-butenyl, 2-butenyl, 2-methylpropenyl, 2-pentenyl, 3-hexenyl and so on, which may be optionally substituted with a carboxy or a sulfo group.

The expression "a nitrogen containing 5–6 membered heterocyclic ring which may contain 1 to 3 further heteroatoms selected from N, S and O" according to the present invention includes unsaturated, partially saturated and wholly saturated ring systems such as pyridine, pyrimidine, pyrazine, pyrrolidine, piperidine, piperazine, oxazole, oxazoline, oxazolidine, pyrazoline, pyrazolidine, thiazolidine, morpholine, thiomorpholine, pyrrole, pyrroline, imidazole, imidazolidine, thiadiazole, oxadiazole and tetrazole.

In said "nitrogen containing 5–6 membered heterocyclic ring" 1 to 3 ring carbons may optionally bear a group carboxy, sulfo, carboxy$(C_1-C_4)$alkyl and sulfo$(C_1-C_4)$alkyl and the ring nitrogen atom may optionally be substituted by $(C_1-C_4)$alkyl, carboxy$(C_1-C_4)$alkyl, sulfo$(C_1-C_4)$alkyl, and benzyl, The expression "fully saturated 5–7 membered nitrogen containing heterocyclic ring wherein the nitrogen atom may be optionally substituted by $(C_1-C_4)$alkyl or benzyl" identifies a fully saturated heterocycle of 5–7 members containing a nitrogen atom which can be optionally substituted by $(C_1-C_4)$alkyl or benzyl wherein the carbon skeleton may optionally bear one or two substituents selected from $(C_1-C_4)$alkyl, carboxy and sulfo. Said heterocyclic rings are connected with the nitrogen moiety of the rest

through a bond between the same nitrogen moiety and a carbon atom of the heterocyclic rest. Examples of said radicals are: 1-methyl-4-pyrrolidinyl, 3-piperidinyl, 1-ethyl-4-piperidinyl, 1-benzyl-2,6-dimethyl-4-piperidinyl, and 4-carboxy-1-methyl-2-piperidinyl;

When $R_2$ and $R_3$ taken together with the adjacent nitrogen atom represent "a fully saturated 5–7 membered heterocyclic ring which may optionally contain a further heteroatom selected from O, S and N" this expression includes, for instance, the following heterocyclic groups: pyrrolidino, morpholino, piperidino, piperazino, thiomorpholino, pyrazolidino, 1,3-oxazolidino, 1,3-thiazolidino and hexahydroazepino When the further heteroatom is N it may optionally bear a substituent selected from $(C_1-C_4)$alkyl, benzyl, carboxy, carboxy$(C_1-C_4)$alkyl, sulfo and sulfo$(C_1-C_4)$alkyl.

The term "1-deoxy-1-glucityl" identifies a compound of formula (I) wherein Y is a radical deriving from glucamine, i.e. 1-amino-1-deoxy-glucitol. The term "2-deoxy-2-glucosyl" identifies a compound of formula (I) wherein Y is a radical deriving from glucosamine, i.e. 2-amino-2-deoxy-glucose.

A preferred group of compounds of the invention is represented by those compounds of formula I wherein R represents methoxymethyl, $R_1$ and $R_4$ represent a methyl group and the other substituents are as defined above.

A further preferred group of compounds of the invention are those compounds of formula I wherein R represents methoxymethyl, $R_1$ and $R_4$ represent a methyl group, and Y represents a group of formula

wherein $R_2$ is hydrogen and $R_3$ is defined as above.

A further preferred group of compounds of the invention is represented by those compounds of formula I wherein R is methoxymethyl, $R_1$ and $R_4$ represent a methyl group and Y is an amino moiety which derive from a natural amino acid such as for example glycine, ornithine, serine, aspartic acid, tyrosine, leucine, phenylalanine, methionine, proline, threonine, lysine, or a synthetic dipeptide such as glycyllysine, serylproline, glycylprolinamide, tyrosylprolinamide, threonylprolinamide, leucylprolinamide.

A further preferred group of compounds comprises those compounds of formula I wherein R is methoxymethyl, $R_1$ and $R_4$ are methyl, Y is a group $NR_2R_3$ wherein $R_2$ is hydrogen and $R_3$ is a linear alkyl chain preferably of 3 to 12 carbons, more preferably of 3 to 7 carbons substituted with a group selected from COOH, $SO_3H$ and $PO_3H_2$.

The most preferred compound is represented the formula I wherein R is methoxymethyl, $R_1$ and $R_4$ are methyl and Y is a group $NR_2R_3$ wherein $R_2$ is hydrogen and $R_3$ is $CH_2CH_2CH_2CH_2CH_2$—COOH.

A further preferred group of compounds of the invention are those compounds of formula I wherein R represents hydrogen, hydroxymethyl and methoxymethyl, $R_1$ represents hydrogen or a methyl group, and Y represents a group of formula

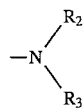

wherein $R_2$ is hydrogen and $R_3$ and $R_4$ are defined as above.

A further preferred group of compounds of the invention is represented by those compounds of formula I wherein R is hydrogen, hydroxymethyl or methoxymethyl, $R_1$ represents hydrogen or a methyl group, $R_4$ is hydrogen, methyl or hydroxymethyl with the proviso that when $R_4$ is hydrogen or hydroxymethyl then R is methoxymethyl and $R_1$ is methyl, and Y is an amino moiety which derive from a natural amino acid such as for example glycine, ornithine, serine, aspartic acid, tyrosine, leucine, phenylalanine, methionine, proline, threonine, lysine, or a synthetic dipeptide such as glycyllysine, serylproline, glycylprolinamide, tyrosylprolinamide, threonylprolinamide, leucylprolinamide.

A further preferred group of compounds comprises those compounds of formula I wherein R is hydrogen, hydroxymethyl or methoxymethyl, $R_1$ is hydrogen or methyl, $R_4$ is hydrogen, methyl or hydroxymethyl with the proviso that when $R_4$ is hydrogen or hydroxymethyl then R is methoxymethyl and $R_1$ is methyl, Y is a group $NR_2R_3$ wherein $R_2$ is hydrogen and $R_3$ is a linear alkyl chain preferably of 3 to 12 carbons, more preferably of 3 to 7 carbons substituted with a group selected from COOH, $SO_3H$ and $PO_3H_2$.

The last preferred group of compounds is represented by the formula I wherein R hydrogen, hydroxymethyl or methoxymethyl, $R_1$ is hydrogen or methyl, $R_4$ is as defined above and Y is a group $NR_2R_3$ wherein $R_2$ is hydrogen and $R_3$ is $CH_2CH_2CH_2CH_2CH_2$—COOH.

Representative examples of the compounds of the invention, include those compounds of formula I wherein R, $R_1$, $R_4$ and Y are as defined above and

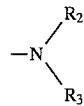

represents

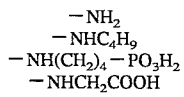

—continued
—NH—$CH_2CONH_2$
—NH—$CH_2$—$CON(C_2H_5)_2$

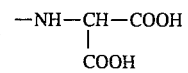

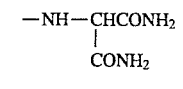

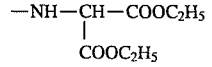

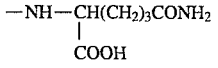

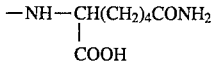

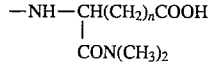

wherein n is 2, 3 or 4
—NH—$(CH_2)_n$—$NH_2$
—NH—$(CH_2)_n$—$NHCH_3$
—NH—$(CH_2)_n$—$N(CH_3)_2$
—NH—$(CH_2)_n$—$N(C_2H_5)_2$
—HN—$(CH_2)_n$—$N(CH_3)(C_2H_5)$
wherein n is 2, 3, 4, 5, 6, 7 or 8

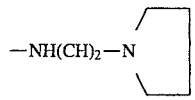

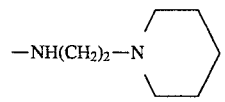

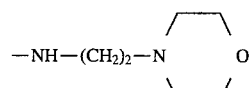

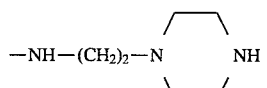

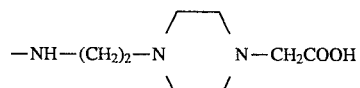

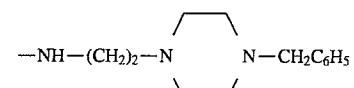

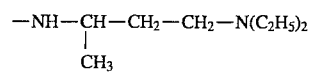

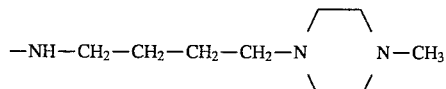

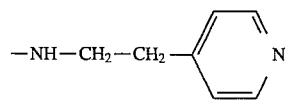

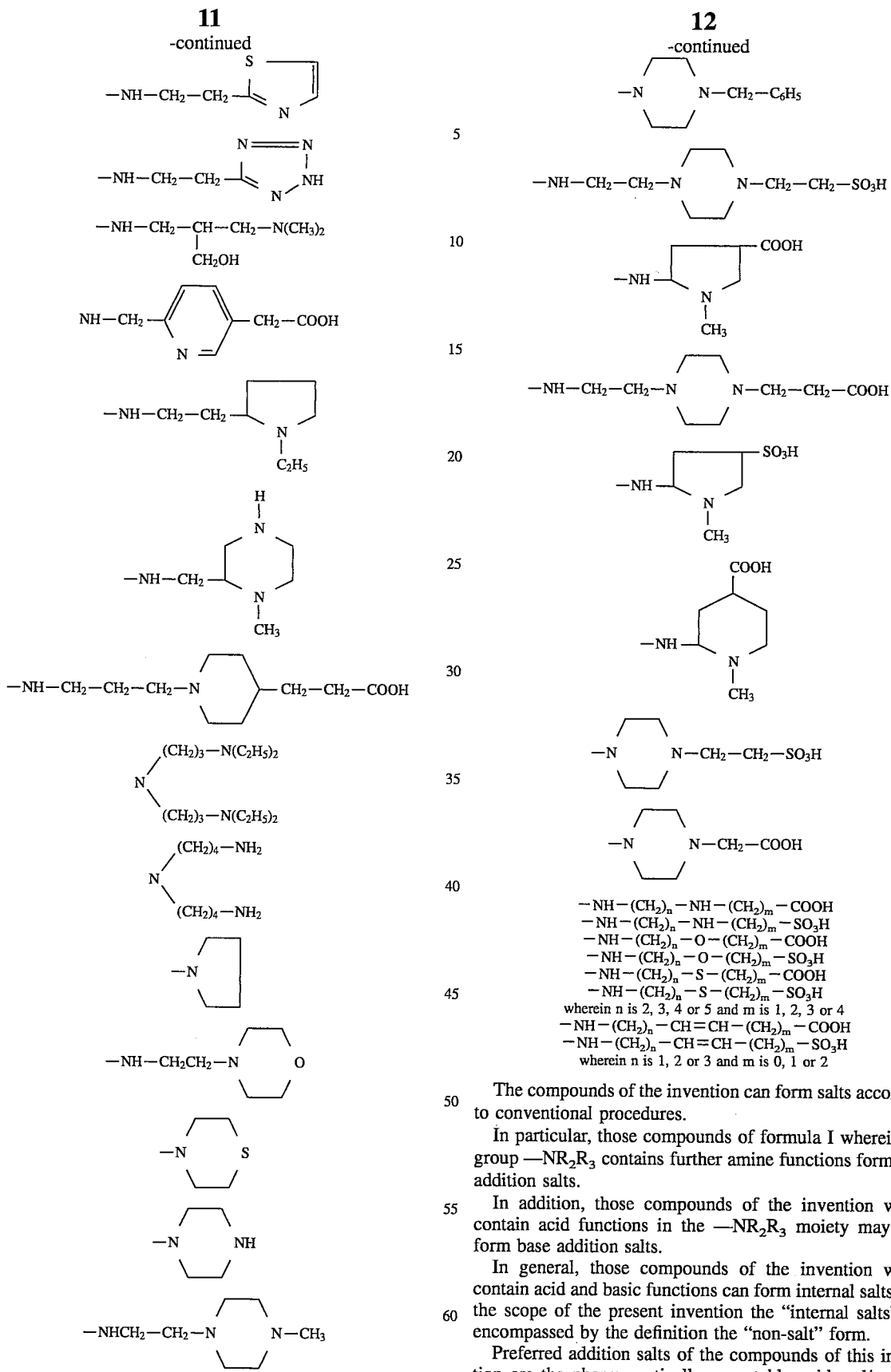

wherein n is 2, 3, 4 or 5 and m is 1, 2, 3 or 4

$-NH-(CH_2)_n-CH=CH-(CH_2)_m-COOH$
$-NH-(CH_2)_n-CH=CH-(CH_2)_m-SO_3H$ wherein n is 1, 2 or 3 and m is 0, 1 or 2

The compounds of the invention can form salts according to conventional procedures.

In particular, those compounds of formula I wherein the group —$NR_2R_3$ contains further amine functions form acid addition salts.

In addition, those compounds of the invention which contain acid functions in the —$NR_2R_3$ moiety may also form base addition salts.

In general, those compounds of the invention which contain acid and basic functions can form internal salts. For the scope of the present invention the "internal salts" are encompassed by the definition the "non-salt" form.

Preferred addition salts of the compounds of this invention are the pharmaceutically acceptable acid and/or base addition salts.

With the term "pharmaceutically acceptable acid and/or base addition salts" are intended those salts with acids and/or bases which from biological, manufacturing and formulation standpoint are compatible with the pharmaceutical practice as well as with the use in the animal growth promotion.

Representative and suitable acid addition salts of the compounds of formula I include those salts formed by standard reaction with both organic and inorganic acids such as, for example, hydrochloric, hydrobromic, sulfuric, phosphoric, acetic, trifluoroacetic, trichloroacetic, succinic, citric, ascorbic, lactic, maleic, fumaric, palmitic, cholic, pamoic, mucic, glutamic, camphoric, glutaric, glycolic, phthalic, tartaric, lauric, stearic, salicylic, methanesulfonic, dodecylsulfonic acid (estolic acid), benzenesulfonic, sorbic, picric, benzoic, cinnamic and the like acids.

Representative examples of these bases are: alkali metal or alkaline-earth metal hydroxide such sodium, potassium, and calcium hydroxide; ammonia and organic aliphatic, alicyclic or aromatic amines such as methylamine, dimethylamine, trimethylamine, 2-amino-2-hydroxymethyl-1,3-propanediol (TRIS), picoline and basic aminoacids such as lysine, ornithine, arginine and histidine.

The transformation of the free amino or non-salt compounds of the invention into the corresponding addition salts, and the reverse, i.e. the transformation of an addition salt of a compound of the invention info the non-salt or free amino form, are within the ordinary technical skill and are encompassed by the present invention.

For instance, a compound of formula I can be transformed into the corresponding acid or base addition-salt by dissolving the non-salt form in an aqueous solvent and adding a slight molar excess of the selected acid or base. The resulting solution or suspension is then lyophilized to recover the desired salt. Instead of lyophilizing, in some instances, it is possible to recover the final salt by extraction with an organic solvent, concentration to a small volume of the separated organic phase and precipitation by adding a non-solvent.

In case the final salt is unsoluble in an organic solvent where the non-salt form is soluble it is recovered by filtration from the organic solution non-salt form after addition of the stoichiometric amount or a slight molar excess of the selected acid base.

The non-salt form can be prepared from a corresponding acid or base salt dissolved in an aqueous solvent which is then neutralized to free the non-salt form. This is then recovered for instance by extraction with an organic solvent or is transformed into another base or acid addition salt by adding the selected acid or base and working up as above.

When following the neutralization desalting is necessary, a common desalting procedure may be employed.

For example, column chromatography on controlled pore polydextrane resins (such as Sephadex LH 20) or silanized silica gel may be conveniently used. After eluting the undesired salts with an aqueous solution, the desired product is eluted by means of linear gradient or step-gradient of a mixture of water and a polar or apolar organic solvent, such as acetonitrile/water from 50:50 to about 100:1% acetonitrile.

As is known in the art, the salt formation either with pharmaceutically acceptable acids (bases) or non-pharmaceutically acceptable acids (bases) may be used as a convenient purification technique. After formation and isolation, salt form of a compound of formula I can be transformed into the corresponding non-salt or into a pharmaceutically acceptable salt.

In some instances the acid addition salt of a compound of formula I is more soluble in water and hydrophilic solvents and has an increased chemical stability.

However, in view of the similarity of the properties of the compounds of formula I and their salts, what is said in the present application when dealing with the biological activities of the compounds of formula I applies also to their pharmaceutically acceptable salts, and viceversa.

In view of their properties, the compounds of the invention can be used as active ingredients in the preparation of medicaments for human or animal treatment.

In particular, the amide derivatives of the antibiotic GE 2270 compounds of formula I are antimicrobial agents mainly active against gram positive bacteria and gram positive as well as gram negative anaerobes.

A general procedure for preparing a compound of this invention is represented by the reaction (amidation) of a suitable antibiotic GE 2270 compound having formula (II)

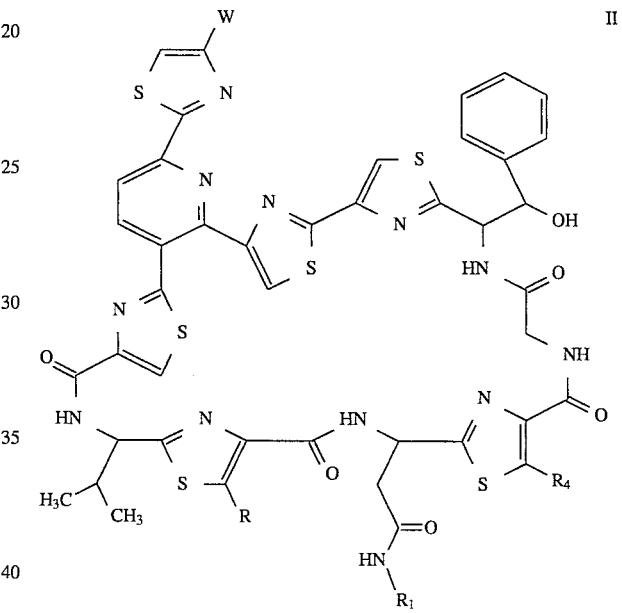

wherein

W represents a carboxy or an activated ester function;

R represents hydrogen, hydroxymethyl or methoxymethyl;

$R_1$ represents hydrogen or methyl;

$R_4$ represents hydrogen, methyl or hydroxymethyl, with the proviso that, when $R_4$ represents hydrogen or hydroxymethyl, then simultaneously R is methoxymethyl and $R_1$ is methyl; with a selected amine of formula $HNR_2R_3$ wherein $R_2$ and $R_3$ have the same meanings as above in an inert organic solvent and, when W is carboxy, in the presence of a condensing agent.

In carrying out the amidation for preparing the compounds of this invention, sometimes, it is convenient to protect the functions of the reactants which are not involved in the amidation reaction but could result sensitive to the reaction conditions or negatively affect the reaction course, for instance, yielding undesired side-product.

Furthermore, when the amino acid contains further reactive functions such as amino, carboxy or mercapto groups which may interfere with the course of the amidation, these are protected by means of methods known per se in the art such as those described in references books like E. Gross and J. Meienhofer "The Peptides", Vol. 3, Academic Press, New York, 1981 and M. Bodanszky and A. Bodanszky "The Practice of Peptide Synthesis, Springer-Verlag, Berlin Heidelberg, 1984. These protecting groups must be stable at the conditions the amidation reaction takes place and must be easily removable at the end of the reaction without affecting either the newly formed amide bond or any other part of the molecule.

Representative examples of N-protecting groups which may be advantageously used in the process of the invention for protecting an amino function are carbamate forming reagents characterized by the following oxycarbonyl groups: 1,1-dimethylpropynyl-oxycarbonyl, t-butyloxycarbonyl, vinyloxycarbonyl, aryloxycarbonyl, cinnamyloxycarbonyl, benzyloxycarbonyl, p-nitrobenzyloxycarbonyl-3,4-dimethoxy-6-nitrobenzyloxycarbonyl, 2,4-dichlorobenzyloxycarbonyl, 5-benzisoxazolylmethyloxycarbonyl, 9-anthranylmethyloxycarbonyl, diphenylmethyloxycarbonyl, isonicotinyloxycarbonyl, diphenylmethyloxycarbonyl, isonicotinyloxycarbonyl, S-benzyloxycarbonyl, and the like.

A suitable protection for reactive carboxylic acid function is, for instance, by forming an ester function.

The man skilled in the art is capable, also on the basis of the present disclosure, of deciding which functions of the amine $HNR_2R_3$ need to be protected, how they must be protected and the proper deprotection reaction which is necessary to free the final compound.

As it is appreciated by the skilled technician, the ultimate choice of the specific protecting group depends on the characteristics of the particular amide derivative which is desired. In fact, this amide function of the final compound should be stable at the condition of removal of the protecting group(s).

Since the conditions of removal of the different protecting groups are known, the skilled technician capable of selecting the proper protecting group.

Inert organic solvents useful for the condensation reaction are those solvents which do not unfavorably interfere with the reaction course and are capable of at least partially solubilizing the antibiotic starting material.

Examples of said inert solvents are organic amides, ethers of glycols and polyols, phosphoramides, sulfoxides. Preferred examples of inert solvents are: dimethylformamide, dimethoxyethane, hexamethylphosphoramide, dimethylsulfoxide, dioxane, and mixtures thereof.

Sometimes, water is compatible with the reaction conditions.

The condensing agent in the process of the invention when W is carboxy is one suitable for forming amide bonds in organic compounds and in particular peptide synthesis.

Representative and preferred examples of condensing agents are $(C_1-C_4)$alkyl, phenyl or heterocyclic phosphorazidates such as, diphenylphosphorazidate (DPPA), diethyl-phosphorazidate, di(4-nitrophenyl)phosphorazidate, dimorpholylphosphorazidate and diphenylphosphorochloridate or benzotriazol-1-yl-oxy-tripyrrolidinophosphonium-hexafluorophosphate (PyBOP). The preferred condensing agent is diphenyl phosphorazidate (DPPA).

In the process of the invention, the amine reactant $HNR_2R_3$ is normally used in a slight molar excess.

In general, a 1- to 2-fold molar excess is used while a 1.2- to 1.5-fold molar excess is preferred.

For the amidation to proceed, it is necessary that the amine $HNR_2R_3$ be capable of forming a salt wish the carboxy function of the antibiotic starting material. In case the amine $HNR_2R_3$ is not strong enough to form such a salt in the selected reaction medium, it is necessary to add a salt-forming base to the reaction mixture at least in an equimolecular amount with the antibiotic starting material.

Examples of said salt-forming bases are tertiary organic aliphatic or alicyclic amines such as trimethylamine, triethylamine, N-methyl pyrrolidine or heterocyclic bases such as picoline, and the like.

The condensing agent is generally employed in a slight molar excess such as from 1.1 to 1.5 and preferably is 1.2 times the antibiotic GE 2270 starting compound.

In addition, the amine reactant $HNR_2R_3$ may also conveniently be introduced in the reaction medium as corresponding acid addition salt, e.g. the hydrochloride. In this case, at least a double molar proportion and preferably a 2 to 3 fold molar excess of a strong base capable of freeing the $HNR_2R_3$ amine from its salts, is used. Also in this case, the suitable base is a tertiary organic aliphatic or alicyclic amine like those exemplified above. In fact, at least in some instances, the use of salt of the amine $HNR_2R_3$, which then freed in situ with the above mentioned bases, is greatly preferred especially when the salt is more stable than the corresponding free amine.

The reaction temperature will vary considerably depending on the specific starting materials and reaction conditions. In general, it is preferred to conduct the reaction at temperatures between 0°–20° C.

Also the reaction time vary considerably depending on the other reaction parameters. In general the condensation reaction is completed in about 5–24 h.

In any case, the reaction course is monitored by TLC or preferably by HPLC according to methods known in the art.

On the basis of the results of these assays a man skilled in the art will be able to evaluate the reaction course and decide when to stop the reaction and start working up the reaction mass according to known per se techniques which include, for instance, extraction with solvents, precipitation by addition non-solvents, etc., in conjunction with further separations and purifications by column chromatography.

As already said, when protection of the $HNR_2R_3$ reactant is necessary, the protected final compound then de-protected according to procedures which are known per se and mainly depends on the protecting group involved.

When an activated ester is used as the GE 2270 starting material, said ester is one wherein the esterified alcohol is providing a leaving group which can be readily displaced and substituted by the amine $HNR_2R_3$ under reaction conditions which do not modify the other portions of the molecule. The amine reactant is usually employed in a molar excess over the activated ester in a solvent which is selected from those mentioned above and the lower alkanols. The reaction temperature generally ranges between 0° C. and 100° C. Examples of the activated ester include lower alkyl esters wherein the lower alkyl moiety is optionally substituted by cyano and nitro, phenyl esters substituted by halo and nitro groups as well as the ester moiety contained in GE 2270 factor $A_2$.

It is evident that in many instances a compound of the invention may be prepared in more than one way and that a compound of the invention may be transformed into another by means of known per se reactions.

For instance when the $HNR_2R_3$ amine contains a carboxy or an ester function which can be further converted into the corresponding amide derivative, a desired compound of formula I may be prepared by condensing first said amine with the selected GE 2270 starting material and then converting the carboxy or ester function to amide by reaction with the appropriate amine.

The following tables list the structure formulas of some representative compounds of the invention (TABLE I) and their methods of preparation, (described in details in the Experimental Section), starting materials and reaction yields (TABLE II).

TABLE I

| COMPOUND OF EXAMPLE NO. | Y | R | $R_1$ | $R_4$ |
|---|---|---|---|---|
| 1 | $-NHCH_2COOH$ | $CH_2O-CH_3$ | $CH_3$ | $CH_3$ |
| 2 | $-NHCHCOOH$ \| $CH_2CH_2CH_2NH_2$ | $CH_2O-CH_3$ | $CH_3$ | $CH_3$ |
| 3 | $-NHCHCOOH$ \| $CH_2OH$ | $CH_2O-CH_3$ | $CH_3$ | $CH_3$ |
| 4 | $-NHCHCOOH$ \| $CH_2COOH$ | $CH_2O-CH_3$ | $CH_3$ | $CH_3$ |
| 5 | $-NHCH-COOH$ \| $CH_2-C_6H_4-OH$ | $CH_2O-CH_3$ | $CH_3$ | $CH_3$ |
| 6 | $-NHCHCOOH$ \| $CH_2CH(CH_3)_2$ | $CH_2O-CH_3$ | $CH_3$ | $CH_3$ |
| 7 | $-NHCH-COOH$ \| $CH_2-C_6H_5$ | $CH_2O-CH_3$ | $CH_3$ | $CH_3$ |
| 8 | $-NHCHCOOH$ \| $CH_2CH_2SCH_3$ | $CH_2O-CH_3$ | $CH_3$ | $CH_3$ |
| 9 | $-N$(pyrrolidine-2-COOH) | $CH_2O-CH_3$ | $CH_3$ | $CH_3$ |
| 10 | $-NHCHCOOH$ \| $CH(OH)CH_3$ | $CH_2O-CH_3$ | $CH_3$ | $CH_3$ |
| 11 | $-NHCH_2CH_2CH_2CH_2CH-COOH$ \| $NH_2$ | $CH_2O-CH_3$ | $CH_3$ | $CH_3$ |
| 12 | $-NHCH_2CONHCHCOOH$ \| $CH_2CH_2CH_2CH_2NH_2$ | $CH_2O-CH_3$ | $CH_3$ | $CH_3$ |
| 13 | $-NHCHCON$(pyrrolidine-2-COOH) \| $CH_2OH$ | $CH_2O-CH_3$ | $CH_3$ | $CH_3$ |
| 14 | $-NHCH_2CON$(pyrrolidine-2-$CONH_2$) | $CH_2O-CH_3$ | $CH_3$ | $CH_3$ |
| 15 | $-NHCHCON$(pyrrolidine-2-$CONH_2$) \| $CH_2-C_6H_4-OH$ | $CH_2O-CH_3$ | $CH_3$ | $CH_3$ |

TABLE I-continued

| COMPOUND OF EXAMPLE NO. | Y | R | R₁ | R₄ |
|---|---|---|---|---|
| 16 | −NHCHCON(pyrrolidine-CONH₂), with CH₃CHOH on α-carbon | $CH_2O-CH_3$ | $CH_3$ | $CH_3$ |
| 17 | −NHCHCON(pyrrolidine-CONH₂), with CH₂CH(CH₃)₂ on α-carbon | $CH_2O-CH_3$ | $CH_3$ | $CH_3$ |
| 18 | −NHCH₂CH₂CH₂COOH | $CH_2O-CH_3$ | $CH_3$ | $CH_3$ |
| 19 | −NHCH₂CH₂CH₂CH₂CH₂COOH | $CH_2O-CH_3$ | $CH_3$ | $CH_3$ |
| 20 | −NHCH₂CH₂CH₂CH₂CH₂CH₂CH₂COOH | $CH_2O-CH_3$ | $CH_3$ | $CH_3$ |
| 21 | −NHCH₂CH₂CH₂CH₂CH₂CH₂CH₂CH₂CH₂COOH | $CH_2O-CH_3$ | $CH_3$ | $CH_3$ |
| 22 | −NHCH₂CH₂SO₃H | $CH_2O-CH_3$ | $CH_3$ | $CH_3$ |
| 23 | −NHCH₂CH₂CH₂SO₃H | $CH_2O-CH_3$ | $CH_3$ | $CH_3$ |
| 24 | −NHCH₂CH₂CH₂PO₃H₂ | $CH_2O-CH_3$ | $CH_3$ | $CH_3$ |
| 25 | −NHCH₂CH₂CH₂CH₂CH₂PO₃H₂ | $CH_2O-CH_3$ | $CH_3$ | $CH_3$ |
| 26 | −NHCH₂−(C₆H₄)−COOH | $CH_2O-CH_3$ | $CH_3$ | $CH_3$ |
| 27 | −N(piperidine-4-COOH) | $CH_2O-CH_3$ | $CH_3$ | $CH_3$ |
| 28 | −NHCH₂CH₂CH₂CH₂−(tetrazole) | $CH_2O-CH_3$ | $CH_3$ | $CH_3$ |
| 29 | −N(CH₃)−CH₂CH(OH)CH(OH)CH(OH)CH₂OH | $CH_2O-CH_3$ | $CH_3$ | $CH_3$ |
| 30 | −NH−(2-amino-2-deoxyglucopyranose) | $CH_2O-CH_3$ | $CH_3$ | $CH_3$ |
| 31 | −NHCH₂CH₂CH₂NHCO−(3,4-dihydroxyphenyl) | $CH_2O-CH_3$ | $CH_3$ | $CH_3$ |
| 32 | −NHCH₂CH₂N(CH₃)₂ | $CH_2O-CH_3$ | $CH_3$ | $CH_3$ |
| 33 | −NH−(1-benzylpiperidin-4-yl) | $CH_2O-CH_3$ | $CH_3$ | $CH_3$ |
| 34 | −N(CH₂CH₂CH₂NH₂)(CH₂CH₂CH₂CH₂NH₂) | $CH_2O-CH_3$ | $CH_3$ | $CH_3$ |
| 35 | −NH₂ | $CH_2O-CH_3$ | $CH_3$ | $CH_3$ |
| 36 | −NHCH₂CH₂CH₂NH₂ | $CH_2O-CH_3$ | $CH_3$ | $CH_3$ |
| 37 | −NHCH₂CHO | $CH_2O-CH_3$ | $CH_3$ | $CH_3$ |

TABLE I-continued

| COMPOUND OF EXAMPLE NO. | Y | R | $R_1$ | $R_4$ |
|---|---|---|---|---|
| 38 | $-NHCH_2CH_2NHCH_2CH_2COOH$ | $CH_2O-CH_3$ | $CH_3$ | $CH_3$ |
| 39 | $-NHCH_2CH_2SCH_2CH_2COOH$ | $CH_2O-CH_3$ | $CH_3$ | $CH_3$ |
| 40 | $-NHCH_2CH_2CH_2CH=CHCOOH$ | $CH_2O-CH_3$ | $CH_3$ | $CH_3$ |
| 41 | $-NHCH_2CH_2OCH_2CH_2COOH$ | $CH_2O-CH_3$ | $CH_3$ | $CH_3$ |
| 42 | $-NHCH_2CH_2CH_2CH_2CH_2COOH$ | $CH_2O-CH_3$ | $CH_3$ | $CH_2OH$ |
| 43 | $-NHCH_2CH_2CH_2CH_2CH_2COOH$ | H | H | $CH_3$ |
| 44 | $-NHCH_2CH_2CH_2CH_2CH_2COOH$ | $CH_2OH$ | $CH_3$ | $CH_3$ |

Compounds No. 2, 11, 12, 34, 36 were isolated as trifluoroacetate salts

TABLE II

| COMPOUND OF EXAMPLE NO. | STARTING MATERIALS (GE 2270 FACTOR + AMINE REACTANT) | METHOD | OVERALL YIELD |
|---|---|---|---|
| 1 | $A_3$ + $HCl.NH_2CH_2COOEt$ | $A_1$ | 80% |
| 2 | $A_3$ + $HCl.NH_2CHCOOMe$ with $CH_2CH_2CH_2NH.Cbz$ substituent | $A_1$ | 72% |
| 3 | $A_3$ + $HCl.NH_2CHCOOMe$ with $CH_2OH$ substituent | $A_1$ | 70% |
| 4 | $A_3$ + $HCl.NH_2CHCOOMe$ with $CH_2COOMe$ substituent | $A_1$ | 54% |
| 5 | $A_3$ + $HCl.NH_2CH-COOMe$ with $CH_2$-(4-hydroxyphenyl) substituent | $A_1$ | 70% |
| 6 | $A_3$ + $HCl.NH_2CHCOOMe$ with $CH_2CH(CH_3)_2$ substituent | $A_1$ | 70% |
| 7 | $A_3$ + $HCl.NH_2CHCOOMe$ with $CH_2$-phenyl substituent | $A_1$ | 60% |
| 8 | $A_3$ + $HCl.NH_2CHCOOMe$ with $CH_2CH_2SCH_3$ substituent | $A_1$ | 70% |
| 9 | $A_3$ + HCl.HN (pyrrolidine with COOMe) | $A_1$ | 75% |
| 10 | $A_3$ + $HCl.NH_2CHCOOMe$ with $CH(OH)(CH_3)$ substituent | $A_1$ | 70% |
| 11 | $A_3$ + $NH_2CH_2CH_2CH_2CH_2CH_2CH-COOH$ with NH.Cbz substituent | $B_1$ | 64% |
| 12 | $A_3$ + $TFA.NH_2CH_2CONHCHCOOH$ with $CH_2CH_2CH_2CH_2NH.Cbz$ substituent | $B_1$ | 74% |
| 13 | 3 + HCl.HN (pyrrolidine with COOMe) | $C_1$ | 70% |

TABLE II-continued

| COMPOUND OF EXAMPLE NO. | STARTING MATERIALS (GE 2270 FACTOR + AMINE REACTANT) | METHOD | OVERALL YIELD |
|---|---|---|---|
| 14 | $\underline{1}$ + HN⟨pyrrolidine-CONH$_2$⟩ | C | 83% |
| 15 | A$_3$ + HCl·NH$_2$CHCON⟨pyrrolidine-CONH$_2$⟩ where CH$_2$ is attached to 4-HO-C$_6$H$_4$ | A | 60% |
|  | or |  |  |
|  | $\underline{5}$ + HN⟨pyrrolidine-CONH$_2$⟩ | C | 70% |
| 16 | $\underline{10}$ + HN⟨pyrrolidine-CONH$_2$⟩ | C | 60% |
| 17 | $\underline{6}$ + HN⟨pyrrolidine-CONH$_2$⟩ | C | 65% |
| 18 | A$_3$ + HCl·NH$_2$CH$_2$CH$_2$CH$_2$COOMe | A$_1$ | 73% |
| 19 | A$_3$ + HCl·NH$_2$CH$_2$CH$_2$CH$_2$CH$_2$CH$_2$COOMe | A$_1$ | 77% |
|  | A$_3$ + NH$_2$CH$_2$CH$_2$CH$_2$CH$_2$CH$_2$COOH | B | 70% |
| 20 | A$_3$ + PTSA·NH$_2$CH$_2$CH$_2$CH$_2$CH$_2$CH$_2$CH$_2$CH$_2$COOMe | A$_1$ | 75% |
| 21 | A$_3$ + PTSA·NH$_2$CH$_2$CH$_2$CH$_2$CH$_2$CH$_2$CH$_2$CH$_2$CH$_2$CH$_2$CH$_2$COOMe | A$_1$ | 70% |
| 22 | A$_3$ + NH$_2$CH$_2$CH$_2$SO$_3$H | B | 20% |
| 23 | A$_3$ + NH$_2$CH$_2$CH$_2$CH$_2$SO$_3$H | B | 25% |
| 24 | A$_3$ + NH$_2$CH$_2$CH$_2$CH$_2$PO$_3$H$_2$ | B | 40% |
| 25 | A$_3$ + NH$_2$CH$_2$CH$_2$CH$_2$CH$_2$CH$_2$PO$_3$H$_2$ | B | 35% |
| 26 | A$_3$ + NH$_2$CH$_2$-C$_6$H$_4$-COOH | B | 60% |
| 27 | A$_3$ + HN⟨piperidine-4-COOH⟩ | B | 50% |
| 28 | A$_3$ + NH$_2$CH$_2$CH$_2$CH$_2$CH$_2$CH$_2$-(tetrazole) | B | 65% |
| 29 | A$_3$ + NH—CH$_2$CHCHCHCH$_2$OH with CH$_3$ on N and OH's on the chain | A | 20% |
| 30 | A$_3$ + 2-amino-2-deoxy-glucose·HCl | A | 80% |

TABLE II-continued

| COMPOUND OF EXAMPLE NO. | STARTING MATERIALS (GE 2270 FACTOR + AMINE REACTANT) | METHOD | OVERALL YIELD |
| --- | --- | --- | --- |
| 31 | 36 + [dithiocarbamate-N-C(=O)-benzene-3,4-di-OTHP structure] | $C_1$ | 80% |
| 32 | $A_3$ + $NH_2CH_2CH_2N(CH_3)_2$ | A | 75% |
| 33 | $A_3$ + $NH_2$—[piperidine]—$NCH_2$—[phenyl] | A | 60% |
| 34 | $A_3$ + $NH$($CH_2CH_2CH_2NH.Boc$)$_2$ | $A_1$ | 50% |
| 35 | $A_3$ + $NH_3$ in MeOH | D | 83% |
| 36 | $A_3$ + $NH_2CH_2CH_2CH_2NH.Boc$ | $A_1$ | 70% |
| 37 | $A_3$ + $NH_2CH_2CH(OCH_3)_2$ | $A_1$ | 65% |
| 38 | 37 + $HCl.NH_2CH_2CH_2COOCH_2CH_3$ | $C_1$ | 20% |
| 39 | $A_3$ + $TFA.NH_2CH_2CH_2SCH_2CH_2COOCH_3$ | $A_1$ | 33% |
| 40 | $A_3$ + $TFA.NH_2CH_2CH_2CH_2CH=CH-COOH$ | B | 51% |
| 41 | $A_3$ + $TFA.NH_2CH_2CH_2OCH_2CH_2COOH$ | B | 37% |
| 42 | $C_{2a}$ + $HCl.NH_2CH_2CH_2CH_2CH_2CH_2COOCH_3$ $NH_2CH_2CH_2CH_2CH_2CH_2COOH$ | F G | 40% 35% |
| 43 | $D_1$ + $HCl.NH_2CH_2CH_2CH_2CH_2CH_2COOCH_3$ $NH_2CH_2CH_2CH_2CH_2CH_2COOH$ | H I | 50% 40% |
| 44 | $D_2$ + $HCl.NH_2CH_2CH_2CH_2CH_2CH_2COOCH_3$ $NH_2CH_2CH_2CH_2CH_2CH_2COOH$ | J K | 35% 30% |

TFA = trifluoroacetic acid
PTSA = p-toluenesulfonic acid

HPLC Analysis

The following table (TABLE III) reports the $R_t$ of representative examples of compounds of this invention.

Analysis were run with a Varian model 5000 LC pump equipped with a 10 µl loop injector and a Varian 2050 variable wavelength detector at 254 nm.

Columns:
  Pre-column LiChroCart-LiChrosorb RP-8 (5 µm) followed by a column LiChroCart 125-4 LiChrospher 100 RP-8 (5 µm)

Eluents:
  A 0.05M aq. $HCOONH_4$
  B $CH_3CN$
  C THF

Method A:
  isochratic 44% of B in A
  Flow rate: 0.7 ml/min

Method B:
  isochratic 40% of B in A
  Flow rate 0.7 ml/min

Method C:
  isochratic 38% of B in A
  Flow rates 0.5 ml/min

Method D:
  isochratic 30% of B in A
  Flow rate: 0.7 ml/min

Method E:
  isochratic 38% of B in A
  Flow rates 0.7 ml/min

Method F:
  gradient from 38 to 55% of B in A in 11 min according to the following program

| Time (min) | % B in A |
| --- | --- |
| 0 | 38 |
| 6 | 38 |
| 7 | 45 |
| 10 | 45 |
| 11 | 55 |

Flow rate: 0.7 ml/min

Method G:
  gradient from 38 to 55% of B in A in 25 min according to the following program

| Time (min) | % B in A |
| --- | --- |
| 0 | 38 |
| 6 | 38 |
| 10 | 44 |

27
-continued

| Time (min) | % B in A |
|---|---|
| 15 | 44 |
| 25 | 55 |

Flow rate: 0.7 ml/min

Method H:
isochratic 55% of B in A
Flow rate: 0.7 ml/min

Method I: isochratic 60% of B in A
Flow rate: 0.7 ml/min

Method L:
isochratic 48% of B in A Flow rate: 0.7 ml/min

Method M:
gradient according to the following program:

| Time (min) | % A | % B | % C |
|---|---|---|---|
| 0 | 74 | 10 | 16 |
| 20 | 62 | 19 | 19 |

Flow rate: 0.7 ml/min

TABLE III

| | HPLC Analysis | | |
|---|---|---|---|
| Compound No. | Method | $R_t$ (min) | K |
| 1 | A | 2.56 | 0.92 |
| 2 | B | 4.09 | 1.15 |
| 3 | C | 6.21 | 1.12 |
| 4 | D | 14.70 | 1.79 |
| 5 | E | 5.99 | 1.28 |
| 6 | A | 4.05 | 1.46 |
| 7 | A | 4.52 | 1.63 |
| 8 | A | 3.44 | 1.24 |
| 9 | E | 5.32 | 1.18 |
| 10 | E | 4.22 | 0.90 |
| 11 | F | 14.30 | 3.05 |
| 12 | F | 5.92 | 1.28 |
| 13 | E | 4.99 | 1.04 |
| 14 | G | 14.09 | 3.01 |
| 15 | G | 17.60 | 3.76 |
| 16 | G | 13.77 | 2.94 |
| 17 | G | 23.75 | 5.07 |
| 18 | G | 7.49 | 1.60 |
| 19 | F | 8.84 | 1.89 |
| 20 | G | 17.77 | 3.78 |
| 21 | G | 31.10 | 6.64 |
| 22 | F | 5.01 | 1.07 |
| 23 | F | 4.40 | 0.94 |
| 24 | F | 6.27 | 1.34 |
| 25 | F | 11.17 | 2.39 |
| 26 | F | 29.04 | 6.02 |
| 27 | F | 6.28 | 1.34 |
| 28 | F | 12.14 | 2.59 |
| 29 | F | 8.02 | 1.71 |
| 30 | E | 6.81–7.61 anomeric mixture | 1.45–1.62 anomeric mixture |
| 31 | F | 17.64 | 3.76 |
| 32 | B | 9.64 | 2.70 |
| 33 | H | 15.10 | 7.40 |
| 34 | I | 7.22 | 3.92 |
| 35 | L | 10.28 | 4.11 |
| 36 | F | 19.32 | 4.13 |
| 37 | F | 14.56 | 3.11 |
| 38 | F | 11.00 | 2.35 |
| 39 | F | 9.48 | 2.02 |
| 40 | F | 6.84 | 1.46 |
| 41 | F | 3.95 | 0.84 |
| 42 | M | 17.23 | 1.32* |
| 43 | M | 15.76 | 1.52** |
| 44 | M | 16.64 | 1.50*** |

TABLE III-continued

| | HPLC Analysis | | |
|---|---|---|---|
| Compound No. | Method | $R_t$ (min) | K |
| 19 | M | 20.81 | 1.32 |

K = Relative Retention time
K = Relative Retention time = $R_t$ amide/$R_t$ GE 2270 proper starting material (i.e. the compound of formula II wherein W is COOH)

EXPERIMENTAL SECTION

TABLE IV—N.M.R.

The $^1$H-NMR spectra were recorded with a Bruker spectrometer in DMSO-$d_6$ (hexadeuterodimethylsulfoxide) using TMS as the internal standard (0.00 ppm) [δ, ppm, m] at 250 MHz and/or 500 MHz (s=singlet, br s=broad singlet, d=doublet, dd=doublet of doublets, t=triplet, m=multiplet)

TABLE V—I.R.

The infrared spectra (IR) were recorded with a Perkin Elmer mod. 580 spectrophotometer in nujol mull.

TABLE VI—U.V.

The ultraviolet absorption spectra were recorded with a Perkin Elmer Model 320 spectrometer.

It will be clear to the skilled technician that the data represented in TABLES IV, V and VI below, do not represent all the values of the peaks obtained but only the values of those peaks which permit to characterize the single substance.

TABLE IV

| | N.M.R. Spectra |
|---|---|
| COMPOUND NO. | $^1$H—NMR (DMSOd$_6$) δ(ppm) |
| 1 | 0.84(d, 3H); 0.87(d, 3H); 2.57(s, 3H); 3.39(s, 3H); 3.77(dd, 1H); 3.99(d, 2H); 4.25(dd, 1H); 4.96(s, 2H); 7.36–7.22(m, 7H); 8.28(s, 1H); 8.50(s, 1H); 8.59(s, 1H) |
| 2 | 0.79(d, 3H); 0.85(d, 3H); 2.05–1.70(m, 4H); 2.54(s, 3H); 3.33(s, 3H); 3.65(m, 2H); 3.81(dd, 1H); 4.10 (m, 1H), 4.35(dd, 1H); 4.99(s, 2H); 7.35–7.05(m, 7H); 8.20(s, 1H); 8.42(s, 1H); 8.58(s, 1H) |
| 3 | 0.84(d, 3H); 0.87(d, 3H); 2.58(s, 3H); 3.37(s, 3H); 3.80(dd, 2H); 3,84(dd, 1H); 3.91(dd, 1H); 4.26(dd, 1H); 4.55(m, 1H); 4.97(s, 2H); 7.36–7.20(m, 7H); 8.29(s, 1H); 8.55(s, 1H); 8.59(s, 1H) |
| 4 | 0.85(d, 3H); 0.89(d, 3H); 2.58(s, 3H); 2.90(m, 2H); 3.38(s, 3H); 3.70(dd, 1H); 4.29(dd, 1H); 4.85 (m, 1H); 4.98(s, 2H); 7.40–7.20 (m, 7H); 8.28(s, 1H); 8.52(s, 1H); 8.58(s, 1H) |
| 5 | 0.85(d, 3H); 0.88(d, 3H); 2.58(s, 3H); 3.11(m, 2H); 3.26(br; s, 1H); 3.38(s, 3H); 3.78(dd, 1H); 4.28(dd, 1H)4.64(m, 1H); 4.97(s, 2H); 6.68(d, 1H); 7.09(d, 1H); 7.40–7.20(m, 7H); 8.27(s, 1H); 8.47(s, 1H); 8.59(s, 1H) |
| 6 | 0.84(d, 3H). 0.87(d, 3H); 0.92(d, 3H); 0.95(d, 3H); 1.69(m, 2H); 1.86(m, 1H); 2.57(s, 3H); 3.37(s, 3H); 3.78(dd, 1H); 4.26(dd, 1H); 4.53(m, 1H); 4.97(s, 2H); 7.38–7.20(m, 7H); 8.28(s, 1H); 8.46(s, 1H); 8.59(s, 1H) |
| 7 | 0.84(d, 3H); 0.88(d, 3H); 2.58(s, 3H); 3.20(m, 2H); 3.37(s, 3H); 3.77(dd, 1H); 4.25(dd, 1H); 4.73 (m, 1H); 7.40–7.2(m, 12H); 8.28(s, 1H); 8.47(s, 1H)8.59(s, 1H) |
| 8 | 0.85(d, 3H); 0.89(d, 3H); 2.08(s, 3H); 2.16(m, 2H); 2.56(m, 2H); 2.57(s, 3H); 3.40(s, 3H); 3.79(dd, 1H); 4.27(dd, 1H); 4.61(m, 1H); 5.00(s, 2H); 7.37–7.20(m, 7H); 8.29(s, 1H); 8.52(s, 1H); 8.60(s, 1H) |
| 9 | 0.84(d, 3H); 0.88(d, 3H); 2.45–1.70(m, 4H); 2.58(s, 3H); 3.37(s, 3H); 3.68(m, 2H); 3.78(dd, 1H); 4.10 (m, 1H); 4.27(dd, 1H); 4.49(m, 1H); 7.35–7.22(m, |

TABLE IV-continued

N.M.R. Spectra

| COMPOUND NO. | $^1$H—NMR (DMSOd$_6$) δ(ppm) |
|---|---|
| 10 | 7H); 8.27(s, 1H); 8.50(s, 1H); 8.59(s, 1H) 0.85(d, 3H); 0.88(d, 3H); 1.19(d, 3H); 2.59(s, 3H); 3.39(s, 3H); 3.78(dd, 1H); 4.30(m, 2H); 4.48(dd, 1H); 4.99(s, 2H); 7.4–7.2(m, 7H); 8.33(s, 1H); 8.49(s, 1H); 8.60(s, 1H) |
| 11 | 0.84(d, 3H); 0.88(d, 3H); 1.55–1.35(m, 2H); 1.61 (m, 2H); 1.83(m, 2H); 2.58(s, 3H); 3.34(m, 2H); 3.38(s, 3H); 3.79(dd, 1H); 3.91(br; s, 1H); 4.29 (dd, 1H); 4.97(s, 2H); 7.35–7.13(m, 7H); 8.27(s, 1H); 8.43(s, 1H); 8.59(s, 1H) |
| 12 | 0.85(d, 3H); 0.88(d, 3H); 1.37(m, 2H); 1.70–1.49 (m, 3H); 1.75(m, 1H); 2.58(s, 3H); 2.76(m, 2H); 3.38(s, 3H); 3.78(dd, 1H); 4.03(m, 2H); 4.28(m, 2H); 4.97(s, 2H); 7.35–7.20(m, 7H); 8.28(s, 1H); 8.49(s, 1H); 8.59(s, 1H) |
| 13 | 0.84(d, 3H); 0.88(d, 3H); 1.98–1.82(m, 2H); 2.18 (m, 2H); 2.56(s, 3H); 2.69(dd, 2H); 3.36(s, 3H); 3.85–3.62(m, 3H); 4.31(m, 2H); 4.85(m, 1H); 4.96(s, 2H); 7.38–7.19(m, 7H); 8.24(s, 1H); 8.55(s, 1H); 8.63(s, 1H) |
| 14 | 0.85(d, 3H); 0.88(d, 3H); 1.99–1.82(m, 3H); 2.06 (m, 1H); 2.58(s, 3H); 3.58(m, 1H); 3.67(m, 1H); 3.79(dd, 1H); 4.18(d, 2H); 4.28(dd, 1H); 4.97(s, 2H); 6.93(s, 1H); 7–36–7.28(m, 8H); 8.28(s, 1H); 8.52(s, 1H); 8.59(s, 1H) |
| 15 | 0.85(d, 3H); 0.88(d, 3H); 2.07–1.63(m, 4H); 2.58(s, 3H); 2.99(dd, 1H); 3.09(dd, 1H); 3.38(s, 3H); 3.51 (m, 1H); 3.77(m, 2H); 4.30(m, 2H); 4.89(m, 1H); 4.98(s, 2H); 6.66(d, 1H); 6.95(br; s, 1H); 7.16(d, 1H); 7.39–7.20(m, 8H); 8.23(s, 1H); 8.42(s, 1H); 8.58(s, 1H) |
| 16 | 0.84(d, 3H); 0.87(d, 3H); 1.20(d, 3H); 1.98–1.80 (m, 3H); 2.08(m, 1H); 2.56(s, 3H); 3.36(s, 3H); 3.85–3.71(m, 2H); 4.13(m, 1H); 4.28(dd, 1H); 4.31 (dd, 1H); 4.73(m, 1H); 5.05(d, 1H); 6.89(br; s, 1H); 7.15(br; s, 1H); 7.38–7.19(m, 7H); 8.26(s, 1H); 8.51(s, 1H); 8.56(s, 1H) |
| 17 | 0.84(d, 3H); 0.87(d, 3H); 0.94(d, 3H); 0.98(d, 3H); 2.10–1.62(m, 7H); 2.56(s, 3H); 3.36(s, 3H); 3.65(m, 1H); 3.88–3.70(m, 2H); 4.31(m, 2H); 4.88(m, 1H); 4.96(s, 2H); 6.79(br, s, 1H); 7.18(br; s, 1H); 7.35–7.20(m, 7H); 8.25(s, 1H); 8.48(s, 1H); 8.56(s, 1H) |
| 18 | 0.84(d, 3H); 0.88(d, 3H); 1.81(m, 2H); 2.30(t, 2H); 2.58(s, 3H); 3.35(m, 2H); 3.37(s, 3H); 3.78(dd, 1H); 4.28(dd, 1H); 4.97(s, 2H); 7.35–7.20(m, 7H); 8.27(s, 1H); 8.46(s, 1H); 8.59(s, 1H) |
| 19 | 0.84(d, 3H); 0.87(d, 3H); 1.35(m, 2H); 1.56(m, 4H); 2.22(t, 2H); 2.58(s, 3H); 3.36(m, 2H); 3.38(s, 3H); 3.80(dd, 1H); 4.29(dd, 1H); 4.97(s, 2H); 7.42–7.22(m, 7H); 8.29(s, 1H); 8.45(s, 1H); 8.62(s, 1H) |
| 20 | 0.84(d, 3H); 0.88(d; 3H); 1.31(br; s, 6H); 1.51(m, 2H); 1.57(m, 2H); 2.19(t, 2H); 2.58(s, 3H); 3.32 (m, 2H); 3.37(s, 3H); 3.79(dd, 1H); 4.28(dd, 1H); 4.97(s, 2H); 7.38–7.19(m, 7H); 8.27(s, 1H); 8.45(s, 1H); 8.59(s, 1H) |
| 21 | 0.84(d, 3H); 0.88(d, 3H); 1.41–1.20(m, 12H); 1.47 (m, 2H); 1.57(m, 2H); 2.17(t, 2H); 2.58(s, 3H); 3.29(m, 3H); 3.38(s, 3H); 3.79(dd, 1H); 4.28(dd, 1H); 4.97(s, 2H); 7.38–7.19(m, 7H); 8.27(s, 1H); 8.43(s, 1H); 8.59(s, 1H) |
| 22 | 0.85(d, 3H); 0.87(d, 3H); 2.57(s, 3H); 2.79(t, 2H); 3.37(s, 3H); 3.59(t, 2H); 3.78(dd, 1H); 4.28(dd, 1H); 4.97(s, 1H); 7.41–7.20(m, 7H); 8.27(s, 1H); 8.44(s, 1H); 8.57(s, 1H) |
| 23 | 0.84(d, 3H); 0.87(d, 3H); 1.67(m, 2H); 2.53(t, 2H); 2.57(s, 3H); 3.26(t, 2H); 3.37(s, 3H); 3.78(dd, 1H); 4.28(dd, 1H); 4.97(s, 2H); 7.41–7.26(m, 7H); 8.26 (s, 1H); 8.44(s, 1H); 8.57(s, 1H) |
| 24 | 0.85(d, 3H); 0.88(d, 3H); 1.58(m, 2H); 1.79(m, 2H); 2.58(s, 3H); 3.38(s, 3H); 3.50(m, 2H); 3.78 (dd, 1H); 4.28(dd, 1H); 4.97(s, 2H); 7.38–7.21(m, 7H); 8.27(s, 1H); 8.45(s, 1H); 8.59(s, 1H) |
| 25 | 0.84(d, 3H); 0.88(d, 3H); 1.65–1.35(m, 8H); 4.58(s, |

TABLE IV-continued

N.M.R. Spectra

| COMPOUND NO. | $^1$H—NMR (DMSOd$_6$) δ(ppm) |
|---|---|
| | 3H); 3.38(s, 3H); 3.78(dd, 1H); 4.28(dd, 1H); 4.97 (s, 2H); 7.40–7.20(m, 7H); 8.28(s, 1H); 8.43(s, 1H); 8.59(s, 1H) |
| 26 | 0.85(d, 3H); 0.89(d, 3H); 2.56(s, 3H); 3.36(s, 3H); 3.80(dd, 1H); 4.31(dd, 1H); 4.62(br; s, 2H); 4.96(s, 2H); 7.39–7.15(m, 7H); 7.47(d, 2H); 7.90(d, 2H); 8.26(s, 1H); 8.41(s, 1H); 8.58(s, 1H) |
| 27 | 0.84(d 3H); 0.88(d, 3H); 1.62(br, s, 2H); 1.92(br, s, 2H); 2.58(s, 3H); 2.60(m, 1H); 3.38(s, 3H); 3.79 (dd, 1H); 4.16(m, 2H); 4.29(dd, 1H); 4.38(m, 2H); 7.35–7.19(m, 7H); 8.25(s, 1H); 8.29(s, 1H); 8.57(s, 1H) |
| 28 | 0.85(d, 3H); 0.89(d, 3H); 1.39(m, 2H); 1.61(m, 2H) 1.76(m, 2H); 2.58(s, 3H); 2.88(t, 2H); 3.33(m, 2H); 3.80(dd, 1H); 4.29(dd, 1H); 4.98(s, 2H); 7.34–7.20 (m, 7H)8.26(s, 1H); 8.45(s, 1H); 8.58(s, 1H) |
| 29 | 0.84(d, 3H); 0.88(d, 3H); 2.58(s, 6H); 3.38(s, 3H); 3.70–3.41(m, 5H); 3.89–3.75(m, 2H); 3.98(br; s, 1H); 4.35–4.26(m, 2H); 4.97(s, 2H); 7.35–7.21(m, 7H); 8.26(s, 1H); 8.28(s, 1H); 8.58(s, 1H) |
| 30 | 0.84(d, 3H); 0.88(d, 3H); 2.58(s, 3H); 3.29–3.14 (m, 2H); 3.38(s, 3H); 3.90–3.49(m, 4H); 4.29(dd, 1H); 4.92(m, 1H); 4.97(s, 2H); 5.12(t, 1H); 7.35–7.18(m, 7H); 8.26(m, 1H); 8.51(s, 1H); 8.58(s, 1H) |
| 31 | 0.86(d, 3H); 0.89(d, 3H); 1.81(m, 2H); 2.59(s, 3H); 3.32(m, 4H); 3.39(s, 3H); 3.80(dd, 1H); 4.30(dd, 1H); 4.99(s, 2H); 6.75(d, 1H); 7.41–7.18(m, 9H); 8.28(s, 1H); 8.46(s, 1H); 8.59(s, 1H) |
| 32 | 0.85(d, 3H); 0.88(d, 3H); 2.21(s, 6H); 2.59(s, 3H); 3.38(s, 3H); 3.43(m, 4H); 3.81(dd, 1H); 4.31(dd, 1H); 4.98(s, 2H); 7.45–7.19(m, 7H); 8.28(s, 1H); 8.45(s, 1H); 8.61(s, 1H) |
| 33 | 0.86(d, 3H); 0.90(d, 3H); 1.91–1.70(m, 2H); 2.26–2.05(m, 2H); 2.60(s, 3H); 2.91–2.69 (m, 4H); 3.40 (s, 3H); 3.51(br; s, 2H); 3.95–3.75(m, 2H); 4.30 (dd, 1H); 4.99(s, 2H); 7.41–7.18(m, 12H); 8.28(s, 1H)8.45(s, 1H); 8.66(s, 1H) |
| 34 | 0.85(d, 3H); 0.89(d, 3H); 1.81–1.49(m, 4H); 2.01–1.88(m, 2H); 2.59(s, 3H); 2.98–2.65(m, 4H); 3.39(s, 3H); 3.80–3.51(m, 4H); 3.81(dd, 1H); 4.31(dd, 1H); 4.99(s, 2H); 7.41–7.18(m, 7H); 7.90–7.65(m, 6H); 8.25(s, 1H); 8.36(s, 1H); 8.61(s, 1H) |
| 35 | 0.85(d, 3H); 0.88(d, 3H); 2.59(s, 3H); 3.39(s, 3H); 3.79(dd, 1H); 4.29(dd, 1H); 4.98(s, 2H); 7.40–7.19 (m, 7H); 7.72(br, s, 1H); 8.03(br, s, 1H); 8.28(s, 1H); 8.47(s, 1H); 8.60(s, 1H) |
| 36 | 0.85(d, 3H); 0.88(d, 3H); 1.87(m, 2H); 2.54(s, 3H); 2.89(m, 2H); 3.37(s, 3H); 3.42(m, 2H); 3.79 (dd, 1H); 4.29(dd, 1H); 4.98(s, 2H); 7.38–7.20(m, 7H); 7.69(br; s, 3H); 8.29(s, 1H); 8.49(s, 1H); 8.61 (s, 1H) |
| 37 | 0.83(d, 3H); 0.87(d, 3H); 1.32(m, 1H); 2.16(m, 1H); 2.46(d, 3H); 2.57(s, 3H); 2.71(m, 1H); 3.37(s, 3H); 3.78(dd, 1H); 4.16(d, 1H); 4.26(dd, 1H); 4.67 (m, 1H); 4.96(s, 2H); 6.02(d, 1H); 6.35(dd, 1H); 7.35–7.20(m, 7H); 8.28(s, 1H); 8.49(s, 1H); 8.60(s, 1H); 9.61(s, 1H) |
| 38 | 0.83(d, 3H); 0.87(d, 3H); 1.25(m, 1H); 2.2(m, 1H); 2.5(s, 3H); 2.70(m, 3H); 3.35(s, 3H); 3.63(m, 1H); 3.79(dd, 1H); 4.27(dd, 1H); 4.97(s, 2H); 7.4–7.15 (m, 7H); 8.28(s, 1H); 8.53(s, 1H); 8.61(s, 1H) |
| 39 | 0.83(d, 3H); 0.87(d, 3H); 1.32(m, 1H); 2.16(m, 1H); 2.47(d, 3H); 2.57(s, 3H); 2.72(m, 4H); 3.37 (s, 3H); 3.50(m, 2H); 3.78(dd, 1H); 4.27(dd, 1H); 4.97(s, 2H); 7.40–7.20(m, 7H); 8.28(s, 1H); 8.49(s, 1H); 8.60(s, 1H) |
| 40 | 0.83(d, 3H); 0.87(d, 3H); 1.32(m, 1H); 1.71(m, 2H); 2.25–2.14(m, 2H); 2.46(d, 3H); 2.57(s, 3H); 2.7(m, 1H); 3.37(s, 3H); 3.76(dd, 1H); 4.27(dd, 1H); 4.97(s, 2H); 5.81(d, 1H, J=15.7 Hz); 6.78(m, 1H); 7.39–7.12(m, 7H); 8.28(s, 1H); 8.45(s, 1H); 8.60(s, 1H) |
| 41 | 0.86(d, 3H); 0.89(d, 3H); 1.43(m, 1H); 2.19(m, 1H); 2.47(d, 3H); 2.59(s, 3H); 2.72(m, 1H); 3.39(s, 3H); |

TABLE IV-continued

N.M.R. Spectra

| COMPOUND NO. | $^1$H—NMR (DMSOd$_6$) δ(ppm) |
|---|---|
| | 3.50(t, 2H); 3.58(t, 2H); 3.68(t, 2H); 3.79(dd, 1H); 4.99(s, 2H); 7.42–7.20(m, 7H); 8.27(s, 1H); 8.47 (s, 1H); 8.59(s, 1H) |
| 42 | 0.83(d, 3H); 0.85(d, 3H); 1.2–1.4.(m, 3H); 1.5–1.65 (m, 4H); 2.22(t, 3H); 2.60(d, 1H); 2.69(d, 1H); 3.37(s, 3H); 3.79(dd, 1H); 4.27(dd, 1H); 4.86(m, 2H); 4.97(s, 2H); 5.00(dd, 1H); 5.1–5.4(m, 3H); 5.74(t, 1H); 6.00(d, 1H); 7.2–7.4(m, 7H); 8.27(s, 1H); 8.44(s, 1H); 8.62(s, 1H) |
| 43 | 0.84(d, 3H); 0.89(d, 3H); 1.4–1.2(m, 3H); 1.65–1.50 (m, 4H); 2.23(t, 3H); 2.59(s, 3H); 2.79(m, 1H); 3.87(m, 1H); 4.25(m, 1H); 5.04(t, 1H); 5.35–5.20 (m, 3H); 6.09(d, 1H); 6.67(br, s, 1H); 7.04(br, s, 1H); 7.35–7.15(m, 6H); 8.24(s, 1H); 8.26(s, 1H); 8.45(s, 1H); 8.61(s, 1H) |
| 44 | 0.84(d, 3H); 0.88(d, 3H); 1.4–1.25(m, 3H); 1.65–1.50(m, 4H); 2.23(t, 3H); 2.58(s, 3H); 2.75(m, 1H); 3.78(dd, 1H): 4.28(dd, 1H); 4.98(m, 1H); 5.35–5.15 (m, 3H); 6.03(m, 2H); 7.42–7.15(m, 7H): 8.30(s, 1H): 8.45(s, 1H): 8.62(s, 1H) |

TABLE V

I.R. Spectra

| COMPOUND NO. | I.R. (nujol cm$^{-1}$) |
|---|---|
| 1 | 3370; 3110; 1730; 1655; 1545; 1520 |
| 2 | 3350; 3110; 1720; 1650; 1535; 1500 |
| 3 | 3340; 3105; 1720; 1645; 1535; 1500 |
| 4 | 3360; 1725; 1640; 1535 |
| 5 | 3350; 3110; 1725; 1650; 1535; 1510 |
| 6 | 3370; 3105; 1725; 1655; 1535; 1500 |
| 7 | 3360; 3100; 1725; 1655; 1535; 1490 |
| 8 | 3370; 3105; 1725; 1655; 1535; 1505 |
| 9 | 3370; 3110; 3100; 1725; 1657; 1550; 1530; 1505 |
| 10 | 3370; 3105; 1730; 1655; 1540; 1510 |
| 11 | 3359; 3115; 1653; 1551; 1510; |
| 12 | 3360; 3113; 1720; 1662; 1547; 1510 |
| 13 | 3370; 3110; 1720; 1655; 1530; 1505 |
| 14 | 3350; 3120; 1655; 1535; 1500 |
| 15 | 3350; 3100; 1650; 1530; 1510; |
| 16 | 3340; 3105; 1650; 1530 |
| 17 | 3340; 3100; 1655; 1530 |
| 18 | 3350; 3100; 1710; 1645; 1540 |
| 19 | 3360; 3115; 1720; 1665; 1540; 1506; |
| 20 | 3350; 3113; 1720; 1659; 1549; 1506 |
| 21 | 3340; 1710; 1645; 1540; 1500 |
| 22 | 3304; 1653; 1540 |
| 23 | 3333; 1657; 1547; 1092; 1038; |
| 24 | 3354; 3113; 1653; 1550; 1506; 1245 |
| 25 | 3348; 3111; 1660; 1548; 1507; 1245 |
| 26 | 3315; 1653; 1539; 1238 |
| 27 | 3361; 3113; 1720; 1653; 1531; 1507; 1092 |
| 28 | 3333; 1653; 1547; 1494; 1243 |
| 29 | 3356; 3114; 1653; 1508; 1088 |
| 30 | 3360; 1670; 1505; 1200 |
| 31 | 3351; 3115; 1653; 1549; 1509; 1250 |
| 32 | 3370; 3110; 1655; 1545; 1500; 1245 |
| 33 | 3350; 1655; 1530; 1490; 1220 |
| 34 | 3360; 3105; 1650; 1545; 1510; 1240 |
| 35 | 3320; 1747; 1650; 1540; 1225 |
| 36 | 3330; 1662; 1547; 1496; 1201 |
| 37 | 3327; 1730; 1653; 1464; 1377 |
| 38 | 3355; 1720; 1657; 1543; 1377 |
| 39 | 3321; 1717; 1652; 1545 |
| 40 | 3337; 1665; 1549 |
| 41 | 3341; 1721; 1653; 1548; 1377 |
| 42 | 3335; 1722; 1647; 1543 |
| 43 | 3317; 1665; 1539 |
| 44 | 3317; 1720; 1649; 1545 |

TABLE VI

U.V. DATA λmax ($E_{1cm}^{1\%}$)

| Compound No. | MeOH | HCl 0.1N | Phosphate Buffer pH 7.38 | KOH 0.1N |
|---|---|---|---|---|
| 1 | 309 (290.9) | 312 | 309 (247.9) | 309 (252.7) |
| 2 | 309 (257.5) | 310 (222.6) | 311 | 309 (226.3) |
| 3 | 309 (297.5) | 312 | 309 (229.6) | 309 (235.8) |
| 4 | 309 (245.1) | 312 | 308 (234.7) | 308 (234.1) |
| 5 | 308 (173.8) | 312 | 309 (150.0) | 305 (181.2) |
| 6 | 309 (277.1) | 313 | 309 (229.8) | 309 (236.7) |
| 7 | 309 (258.6) | 313 | 309 (207.9) | 309 (218.9) |
| 8 | 309 (279.8) | 311 | 309 (225.9) | 309 (229.4) |
| 9 | 309 (261.9) | 313 | 308 (228.1) | 309 (235.0) |
| 10 | 309 (279.3) | 314 | 309 (241.8) | 309 (251.1) |
| 11 | 309 (216.8) | 310 (178.5) | 312 | 310 (194.9) |
| 12 | 309 (226.2) | 310 (188.3) | 311 | 309 (202.4) |
| 13 | 308 (237.9) | 314 | 308 (247.4) | 308 (260.3) |
| 14 | 309 (263.4) | 313 | 313 | 314 |
| 15 | 309 (222.6) | 313 | 314 | 304 (169.8) |
| 16 | 309 (235.6) | 313 | 312 | 312 |
| 17 | 309 (230.3) | 312 | 312 | 312 |
| 18 | 309 (288.8) | 313 | 309 (239.4) | 309 (248.0) |
| 19 | 309 (283.2) | 312 | 309 (220.3) | 309 (230.1) |
| 20 | 309 | 314 | 309 | 309 |
| 21 | 309 (271.6) | 313 | 311 (221.6) | 309 (221.6) |
| 22 | 309 (190.9) | 309 (152.2) | 308 (160.4) | 309 (165.6) |
| 23 | 309 (242.2) | 310 (182.2) | 309 (200.9) | 309 (200.9) |
| 24 | 309 | 312 | 310 | 309 |
| 25 | 309 | 312 | 310 | 309 |
| 26 | 309 (260.0) | 313 | 310 (197.7) | 310 (208.6) |
| 27 | 310 (264.6) | 313 | 310 (227.4) | 310 (232.1) |
| 28 | 309 (260.5) | 314 | 310 (186.8) | 310 (203.6) |
| 29 | 309 (243.4) | 311 | 312 | 311 |
| 30 | 309 (248.5) | 311 | 311 | 309 |
| 31 | 305 (253.7) | 310 | 310 | 313 (249.5) |
| 32 | 309 (267.9) | 310 (234.9) | 312 | 312 |
| 33 | 309 (247.5) | 311 (234.4) | 314 | 312 |
| 34 | 310 (224.0) | 309 (198.2) | 310 | 312 |
| 35 | 308 (269.8) | 314 | 313 | 313 |
| 36 | 309 (243.9) | 309 (205.5) | 312 | 313 |
| 37 | 309 (255.1) | 312 | 314 | 312 |
| 38 | 308 | 308 | 308 | 308 |
| 39 | 308 (247.9) | 312 | 308 (201.3) | 308 (215) |
| 40 | 309 (304.3) | 312 | 309 (235.9) | 309 (262.0) |
| 41 | 309 (256.4) | 312 | 309 (215.1) | 309 (228.6) |
| 42 | 309 | 312 | 309 | 307 |
| 43 | 309 (253.6) | 313 | 309 (208.4) | 309 (235.4) |
| 44 | 309 (264.9) | 314 | 309 (208.1) | 309 (223.7) |

The antimicrobial activity of the compounds of the invention can be demonstrated by a series of standard tests in vitro.

MIC for *Propionibacterium aches*, and *Bacteroides fragilis* are determined by agar dilution (inocula $10^4/10^5$ CFU/spot). MIC for other organisms are determined by microbroth dilution (inocula $10^4$ to $10^5$ CFU/ml). Incubation times are 18–24 h, except for *Haemophilus influenzae, P. acnes, B. fragilis* (48 h). All organisms are incubated at 37° C.; *H. influenzae* is incubated in a 5% $CO_2$ atmosphere, anaerobes in an anaerobic gas mixture. Media used are: Iso-Sensitest broth (Oxoid) (Staphylococci, *Streptococcus faecalis, Escherichia coli, Proteus vulgaris*; brain heart infusion broth (Difco)+1% Supplement C (Difco) (*H. influenzae*);

The minimal inhibitory concentrations (MIC, microgram/ml) for some microorganisms are reported below in Table VII.

TABLE VII (MIC, microgram/ml)

| | COMPOUND OF EXAMPLE No. | | | | |
|---|---|---|---|---|---|
| STRAIN | 1 | 2 | 6 | 7 | 8 |
| *Staph. aureus* L165 Tour | 0.5 | 0.13 | <0.13 | 0.25 | 0.25 |
| *Staph. epidermidis* L147 ATCC 12228 | 1 | 0.25 | 1 | 0.5 | 2 |
| *Staph. haemolyticus* L602 | 4 | 16 | 1 | 4 | 2 |
| *Strep. pneumoniae* L44 UC41 | 8 | >128 | 2 | 4 | 4 |
| *Strep. faecalis* L149 ATCC 7080 | 0.25 | 0.06 | <0.13 | >0.13 | 0.25 |
| *Prop. acnes* L1014 ATCC 6919 | <0.13 | 0.06 | <0.13 | <0.13 | <0.13 |
| *Bact. fragilis* L1010 ATCC 23745 | 8 | >128 | >128 | >128 | 32 |
| *Haemophilus Influenzae* type B | 8 | >128 | 32 | 128 | 64 |
| *Esch. coli* L47 SKF 12140 | >128 | >128 | >128 | >128 | >128 |
| *Prot. vulgaris* ATCC 881 | >128 | >128 | >128 | >128 | >128 |

| | COMPOUND OF EXAMPLE No. | | | | |
|---|---|---|---|---|---|
| STRAIN | 14 | 18 | 19 | 20 | 26 |
| *Staph. aureus* L165 Tour | 0.06 | 0.25 | 0.06 | 0.25 | 0.25 |
| *Staph. epidermidis* L147 ATCC 12228 | 0.13 | 0.25 | 0.06 | 0.25 | 0.25 |
| *Staph. haemolyticus* L602 | 0.25 | 1 | 0.25 | 0.25 | 0.5 |
| *Strep. pneumoniae* L44 UC41 | >128 | 1 | 0.25 | 2 | 2 |
| *Strep. faecalis* L149 ATCC 7080 | 0.06 | 0.13 | 0.06 | <0.13 | 0.13 |
| *Prop. acnes* L1014 ATCC 6919 | 0.03 | 0.016 | 0.008 | 0.03 | 0.008 |
| *Bact. fragilis* L1010 ATCC 23745 | >128 | 2 | 4 | >128 | 32 |
| *Haemophilus Influenzae* type B | >128 | 2 | 2 | >128 | 8 |
| *Esch. coli* L47 SKF 12140 | >128 | >128 | >128 | >128 | >128 |
| *Prot. vulgaris* ATCC 881 | >128 | >128 | >128 | >128 | >128 |

| | COMPOUND OF EXAMPLE No. | | | |
|---|---|---|---|---|
| STRAIN | 27 | 28 | 32 | 35 |
| *Staph. aureus* L165 Tour | 0.25 | 0.13 | 0.5 | 0.13 |
| *Staph. epidermidis* L147 ATCC 12228 | 0.5 | 0.5 | 0.5 | 0.13 |
| *Staph. haemolyticus* L602 | 1 | 1 | 0.5 | 0.5 |
| *Strep. pneumoniae* L44 UC41 | 8 | 2 | 1 | >128 |
| *Strep. faecalis* L149 ATCC 7080 | 1 | 0.06 | 0.25 | 0.06 |
| *Prop. acnes* L1014 ATCC 6919 | 0.03 | 0.008 | 0.13 | 0.004 |
| *Bact. fragilis* L1010 ATCC 23745 | 64 | >128 | >128 | >128 |
| *Haemophilus Influenzae* type B | 8 | >128 | >128 | >128 |
| *Esch. coli* L47 SKF 12140 | >128 | >128 | >128 | >128 |
| *Prot. vulgaris* ATCC 881 | >128 | >128 | >128 | >128 |

| | COMPOUND OF EXAMPLE No. | | | | |
|---|---|---|---|---|---|
| STRAIN | 36 | 37 | 38 | 39 | 40 |
| *Staph. aureus* L165 Tour | 0.13 | 0.03 | 32 | 0.13 | 0.25 |
| *Staph. epidermidis* L147 ATCC 12228 | 0.13 | 0.06 | 32 | 0.25 | 0.25 |
| *Staph. haemolyticus* L602 | 0.13 | 0.13 | 64 | 2 | 1 |
| *Strep. pneumoniae* L44 UC41 | 4 | >128 | >128 | 4 | 1 |
| *Strep. faecalis* L149 ATCC 7080 | 0.13 | 0.06 | 16 | ≦0.13 | ≦0.13 |
| *Prop. acnes* L1014 ATCC 6919 | 0.06 | 0.004 | 0.25 | ≦0.13 | — |
| *Bact. fragilis* L1010 ATCC 23745 | >128 | >128 | >128 | 8 | 4 |
| *Haemophilus Influenzae* type B | >128 | >128 | >128 | 1 | 1 |
| *Esch. coli* L47 SKF 12140 | >128 | >128 | >128 | >128 | >128 |
| *Prot. vulgaris* ATCC 881 | >128 | >128 | >128 | >128 | >128 |

| | COMPOUND OF EXAMPLE No. | | | |
|---|---|---|---|---|
| STRAIN | 41 | 42 | 43 | 44 |
| *Staph. aureus* L165 Tour | 0.25 | 0,13 | 0.13 | 0.13 |
| *Staph. epidermidis* L147 ATCC 12228 | 0.5 | 0,13 | 0.5 | 0.5 |
| *Staph. haemolyticus* L602 | 1 | 0.5 | 0.5 | 1 |
| *Strep. pneumoniae* L44 UC41 | 2 | 1 | 0.5 | 1 |
| *Strep. faecalis* L149 ATCC 7080 | ≦0.13 | 0.13 | 0.13 | 0.06 |
| *Prop. acnes* L1014 ATCC 6919 | ≦0.13 | 0.016 | 0.016 | 0.016 |
| *Bact. fragilis* L1010 ATCC 23745 | 4 | >128 | >128 | >128 |
| *Haemophilus Influenzae* type B | 1 | 4 | >128 | >128 |
| *Esch. coli* L47 SKF 12140 | >128 | >128 | >128 | >128 |
| *Prot. vulgaris* ATCC 881 | >128 | >128 | >128 | >128 |

In view of their properties, the compounds the invention can be used as active ingredients in the preparation of medicaments for human or animal treatment.

In particular, the amide derivatives of the antibiotic GE 2270 compounds of formula I are antimicrobial agents mainly active against gram positive bacteria and gram positive as well as gram negative anaerobes.

The main therapeutic indication of the antibiotic substances of the invention is thus in the treatment of infections related to the presence of microorganisms susceptible to them.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compounds of the invention can be administered as such or in admixture with pharmaceutically acceptable carriers and can also be administered in conjunction with other antimicrobial agents. Conjunctive therapy, thus includes sequential, simultaneous and separate administration of the active compounds in a way that the therapeutical effects of the first administered one is not entirely disappeared when the subsequent is administered.

A preferred pharmaceutical formulation is represented by a formulation suitable for a topical application on an intact or damaged skin or mucous membrane. Examples of such formulations are powders, ointments, creams and lotions. The excipients in these formulations are the usual pharmaceutically acceptable vehicles such oleaginous ointment bases (e.g. cetyl esters wax, oleic acid, olive oil, paraffin, spermaceti, starch glycerite); absorbent ointment bases (e.g. anhydrous lanolin, hydrophilic petrolatum), emulsion ointment bases (e.g. cetyl alcohol, glyceryl monostearate, lanolin, stearic acid), water-soluble ointment bases (e.g. glycol ethers and their derivatives which include polyethylene glycols, poly(oxy-1,2-ethan ediyl)-alpha-hydro-omega-hydroxy-octadecanoate, polysorbates, and polyethylene glycols mono-stearates).

These formulations may contain other known excipients, such as preservatives and are prepared as known in the art and reported in reference handbooks such as Remington's Pharmaceutical. Sciences, Seventeenth edition, 1985, Mack Publishing Co.

The compounds of the invention can also be formulated into formulation suitable for parenteral administration according to procedures known per se in the art. For instance, a compound of the invention formulated with polypropylene glycol or dimethylacetamide and a surface-active agent such as polyoxyethylene sorbitan mono-oleate or polyethoxylated castor oil.

A preferred formulation for parenteral administration includes the following excipients: Cremophor® EL (polyoxyl 35 castor oil USP/NF) 20%, propylene glycol 5–10%.

Preferably, this formulation is used for i.v. administration in the treatment of any infection involving a microorganism susceptible to an antibiotic of the invention.

An example of a suitable formulation used for I.V. is the following compound No. 19 100 mg propylene glycol 1 ml water for injection q.s. 5 ml phosphate buffer pH 8–8.5

In the treatment of pseudomembranous colitis or other diseases attributable to the presence of anaerobes in the gastrointestinal tract, an effective dose of the compounds of the invention may be administered orally in suitable pharmaceutical form such as a capsule or an aqueous suspension.

The dosage of the active ingredient depends on many factors which include type, age and conditions of the patient, specific active ingredient and formulation selected for administration, administration schedule, etc.

In general, effective antimicrobial dosages are employed per single unit dosage form. Repeated applications of these dosage forms, e.g. from 2 to 6 times a day, are in general preferred. An effective dosage may be in general in the range 0.5–50 mg/kg body weight/day.

A preferred topic preparation is an ointment containing from 1% to 10% of a compound of the present invention.

Anyway, the prescribing physician will be able to determine the optimal dosage for a given patient in a given situation.

Besides their use as medicaments in human and veterinary therapy, the compounds of the invention can also be used as animal growth promoters.

For this purpose, a compound of the invention is administered orally in a suitable feed. The exact concentration employed is that which is required to provide for the active agent in a growth promotant effective amount when normal amounts of feed are consumed.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and CO., S. Francisco, USA, 1969 or "Livestock Feeds and Feeding" O and B books, Corvallis, Oreg., USA, 1977).

The following examples further illustrate the invention and should not be interpreted as limiting it in any way.

EXAMPLES OF THE INVENTION

PROCEDURE A—Reaction of GE 2270 factor $A_3$ starting material with the selected amine Example 1:

Preparation of compound no. 15, 29, 30, 32, 33

To a stirred solution of 1 mmol of GE 2270 factor $A_3$ (prepared as described in European Patent Application Publication No. 406745) in 10 ml of dimethylformamide (DMF), 1.2 mmols of the selected amine, 1.4 mmols of triethylamine (TEA) and 1.2 mmols of di-phenylphosphorazidate (DPPA) were added at 0° C. (If the salt (chloride, p-toluenesulfonate, etc.) of the selected amine was used, a double amount of TEA had to be used). The temperature was allowed to rise to room temperature and stirring was continued for about 4 h. The reaction mixture was then acidified with 1N aq HCl to about pH 3 and then diluted with water to complete precipitation of the product. The wet solid was dried in air and then purified by flash chromatography on silica gel 60 (230–400 mesh ASTM—Merck) eluting with 3 to 5% methanol in chloroform. Fractions containing the title compound were pooled together and the solvent evaporated. Trituration of the solid with ethyl ether yielded the title compound as a fine powder.

37

PROCEDURE A1—Reaction of GE 2270 factor $A_3$ starting material with the selected amine containing further reactive functional group(s), all of which protected, and subsequent deprotection of the protecting group(s).

Example 2

Preparation of compound no. 34, 36

The reaction was substantially carried out as described in Example 1. Once the reaction product had been purified by flash chromatography, 1 mmol of the solid obtained was treated with 7 ml of cold trifluoroacetic acid (TFA). The suspension was swirled for a few minutes until a solution was obtained and TFA was evaporated "in vacuo" in the cold. The gummy product still containing traces of TFA was then treated with ethyl ether and the title compound was obtained as the trifluoroacetate salt in the form of a fine powder.

Example 3

Preparation of compound no. 1, 3 to 10, 18 to 21, 39

The reaction was substantially carried out as described in Example 1. Once the reaction product had been purified by flash chromatography, 1 mmol of the solid obtained was dissolved in 20 ml of dioxane and 1.2 ml of 1N aq NaOH were added under stirring at room temperature. After 5 h the solution was acidified with 1N aq HCl to pH 2 and diluted with water to complete precipitation of the title compound which was filtered off and allowed to dry in air yielding the title compound as a fine powder.

Example 4

Preparation of compound no. 2

The reaction was carried out as described Example 3. Once hydrolysis of the ester function had been accomplished and the compound had been allowed to dry in air, 1 mmols of the solid obtained was dissolved in 20 ml of TFA and 50 mmols of thioanisole were added under stirring at room temperature as described by Y. Kiso et al., Chem. Pharm. Bull. 28, 673, 1980. After 3.5 h, TFA was evaporated "in vacuo" in the cold and the residue taken up in a minimum amount of 1% methanol in chloroform. Addition of ethyl ether induced the precipitation of the title compound which was filtered, washed with more ethyl ether and dried "in vacuo" to yield the trifluoroacetate salt of the title compound as a fine powder.

Example 4bis

Preparation of compound no. 37

The reaction was substantially carried out as described in Example 1. Once the starting material had disappeared from the reaction mixture, water was added and the precipitate obtained was filtered off, washed with additional water and allowed to dry in air. The crude material was then dissolved in 3 ml of THF and stirred overnight at room temperature in the presence of 10% aq. HCl. Dilution with water provided complete precipitation of the product which was filtered off and allowed to dry in air. The solid was then purified by flash chromatography on silica gel 60 (230–400 mesh ASTM—Merck) eluting with 2 to 4% methanol in chloroform. Fractions containing the title compound were pooled together and the solvent evaporated yielding pale yellow powder.

PROCEDURE B—Reaction of GE 2270 factor $A_3$ starting material with the selected amine containing unprotected acid moieties.

38

Example 5

Preparation of compound no. 19, 22 to 28, 40, 41

1.1 mmol of DPPA were added at 0° C. to a stirred solution of 1 mmol of GE 2270 factor $A_3$ and 1.5 mmols of TEA in 10 ml of DMF. The temperature was allowed to rise to room temperature and stirring was continued for 4.5 more hours. 1.5 Mmols of the selected amine and 2 mmols of TEA were then added to the solution at room temperature and stirring was continued at the same temperature for 5 more hours. (If the selected amine contained more than one acid function, the amount of TEA was adjusted so to free the amino group). The reaction mixture was then acidified with 1N aq HCl to about pH 2 and then diluted with water to complete precipitation of the product. The wet solid was dried in air and then purified by flash chromatography on silica gel 60 (230–400 mesh ASTM—Merck) eluting with 5 to 10% methanol in chloroform. Fractions containing the title compound were pooled together and the solvent evaporated. Trituration of the solid with ethyl ether yielded the title compound as a fine powder.

PROCEDURE B1—Reaction of GE 2270 factor $A_3$ starting material with the selected amine containing reactive functional group(s), all of which are variously protected, in addition to the unprotected acid group(s) and subsequent deprotection of the protecting group(s).

Example 6

Preparation of compound no. 11, 12

The reaction was substantially carried out as described in Example 5. Once the reaction product had been purified by flash chromatography, 1 mmol of the solid obtained was dissolved in 20 ml of TFA and 50 mmols of thioanisole were added under stirring at room temperature. After 3.5 h, TFA was evaporated "in vacuo" in the cold and the residue taken up in a minimum-amount of 1% methanol in chloroform. Addition of ethyl ether induced the precipitation of the title compound which was filtered, washed with more ethyl ether and dried "in vacuo" to yield the trifluoroacetate salt of the title compound as a fine powder.

PROCEDURE C—Reaction of selected amide derivatives of GE 2270 factor $A_3$ as starting material with the selected reagent.

Example 7

Preparation of compound no. 14, 15, 16, 17 from compound no. 1, 5, 10, 6 respectively To a stirred solution of 1 mmol of the appropriate amide derivative of GE 2270 factor $A_3$ (prepared as described in the previous examples) in 10 ml of DMF, 1.2 mmols of the selected amine, 1.4 mmols of TEA and 1.2 mmols of DPPA were added at 0° C. (If the salt (chloride, p-toluenesulfonate, etc.) of the selected amine was used, a double amount of TEA had to be used). The temperature was allowed to rise to room temperature and stirring was continued for about 4 h. The reaction mixture was then acidified with 1N aq HCl to about pH 3 and then diluted with water to complete precipitation of the product. The wet solid was dried in air and then purified by flash chromatography on silica gel 60 (230–400 mesh ASTM—Merck) eluting with 3 to 5% methanol in chloroform. Fractions containing the title compound were pooled together and the solvent evaporated. Trituration of the solid with ethyl ether yielded the title compound as a fine powder.

PROCEDURE C1—Reaction of the selected amide derivative of the GE 2270 factor $A_3$ as starting material with the selected reagent which contains further reactive functional group(s), all of which protected, and subsequent deprotection of the protecting group(s).

Example 8

Preparation of compound no. 13 from compound no. 3

The reaction was carried out as described in Example 7. Once the reaction product had been purified by flash chromatography, 1 mmol of the solid obtained was dissolved in 20 ml of dioxane and 1.2 ml of 1N aq NaOH were added under stirring at room temperature. After 5 h the solution was acidified with 1N aq HCl to pH 2 and diluted with water to complete precipitation of the title compound which was filtered off and allowed to dry in air yielding the title compound as a fine powder.

Example 9

Preparation of compound no. 31 from compound no. 36

To a stirred solution of 1 mmol of the appropriate amide derivative of GE 2270 factor $A_3$ (prepared as described in the previous examples) in 10 ml of 10% methanolic chloroform, 1.2 mmols of TEA and 1.1 mmols the selected reagent (see table —) were added at room temperature. After 20 min the solvent was evaporated "in vacuo" and the residue treated with 5% aq $Na_2CO_3$. The solid obtained was filtered off, washed with more 5% $Na_2CO_3$ and water and finally redissolved in 10 ml of methanol. To this solution, 0.5 ml of water and 0.1 mmols of p-toluenesulfonic acid were added and the reaction mixture was stirred at room temperature overnight. The solution was then reduced to a small volume (about 2 ml) under vacuum and water was added to precipitate the title compound which, after drying in air, was obtained as a fine powder.

Example 9bis

Preparation of compound no. 38 from compound no. 37

To a stirred solution of 0.23 mmols of the appropriate amide derivative of GE 2270 factor $A_3$ (prepared as described in the previous examples) in 40 ml of ethanol, 9.2 mmols of acetic acid, 9.2 mmols of sodium acetate and 0.506 mmols of the selected reagent (see table II) were added at room temperature. After 2 hours 0.46 mmols of $NaBH_4$ (Fluka) were added and stirring was continued overnight at the same temperature. Evaporation of the solvent provided a crude material which was washed with 10 ml of 1N HCl, filtered and allowed to dry in air. The solid was then purified by flash chromatography on silica gel 60 (230–400 mesh ASTM—Merck) eluting with 0 to 10% methanol in dichloromethane. The fractions containing the methyl ester of the title compound (intermediate) were pooled together and the solvent evaporated providing a solid which was redissolved in 2 ml dioxane and treated overnight with a 1.2 molar excess of 1N NaOH at room temperature. Evaporation of the solvent gave a solid a which was further purified by trituration with a mixture of ethyl acetate:methanol yielding the title compound as a fine powder.

PROCEDURE D—Reaction of GE 2270 factor $A_2$ starting material with the selected amine

Example 10

Preparation of compound No. 35

1 mmol of GE 2270 factor $A_2$ (prepared as described in European Patent Application Publication No. 406745) were dissolved in 10 ml of a saturated solution of methanolic ammonia. The solution was allowed to stand for 3 days at room temperature and then evaporated "in vacuo". The residue was taken up in 2 ml of methanol and the title compound precipitated with water, filtered off and allowed to dry in air. Trituration with ethyl ether yielded the title compound as a fine powder.

PROCEDURE E—Preparation of a salt of a compound of the invention.

Example 11

Preparation of the arginine salt of compound No. 19

To a suspension of 3 g of compound No. 19 (2.42 mmols) 180 ml of dioxane, a solution of 423 mg of L-arginine (2.42 mmols) in 120 ml of water were added under stirring and the non clear solution was thus lyophilized to recovered the desired salt.

PROCEDURE F—Reaction of GE 2270 component $C_{2a}$ starting material (i.e. the compound of formula II wherein R is methoxymethyl, $R_1$ is methyl, $R_4$ is hydroxymethyl and W is COOH) with the selected amine is containing further reactive functional group(s), all of which protected, and subsequent deprotection of the protecting group(s).

Example 12

Preparation of compound no. 42

The reaction was carried out as described in Example 3 using GE 2270 component $C_{2a}$ starting material instead of factor $A_3$.

PROCEDURE G—Reaction of GE 2270 component $C_{2a}$ starting material as described in procedure F with the selected amine containing unprotected acid moieties.

Example 13

Preparation of compound no. 42

The reaction was carried out as described in Example 5 using GE 2270 component $C_{2a}$ starting material instead of factor $A_3$.

PROCEDURE H—Reaction of GE 2270 component $D_1$ starting material (i.e. the compound of formula II wherein R and $R_1$ are hydrogen, $R_4$ is methyl and W is COOH) with the selected amine containing further reactive functional group(s), all of which protected, and subsequent deprotection of the protecting group(s).

Example 14

Preparation of compound no. 43

The reaction was carried out as described in Example 3 using GE 2270 component $D_1$ starting material instead of factor $A_3$.

PROCEDURE I—Reaction of GE 2270 component $D_1$ starting material as described in procedure H with the selected amine containing unprotected acid moieties.

Example 15

Preparation of compound no. 43

The reaction was carried out as described in Example 5 using GE 2270 component D1 starting material instead of factor $A_3$.

PROCEDURE J—Reaction of GE 2270 component $D_2$ (i.e. the compound of formula II wherein R is hydroxymethyl, $R_1$ and $R_4$ are methyl and W is COOH) starting material with the selected amine containing further reactive functional group(s), all of which protected, and subsequent deprotection of the protecting group(s).

Example 16

Preparation of compound no. 44

The reaction was carried out as described in Example 3 using GE 2270 component $D_2$ starting material instead of factor $A_3$.

PROCEDURE K—Reaction of GE 2270 component starting material as described in procedure J with the selected amine containing unprotected acid moieties.

Example 17

Preparation of compound no. 44

The reaction was carried out as described in Example 5 using GE 2270 component $D_2$ starting material instead of factor $A_3$.

PROCEDURE L—Reaction of a mixture of minor components ($C_{2a}$, $D_1$, $D_2$ and g) of antibiotic GE 2270 (starting material) with the selected amine containing further reactive functional group(s), all of which protected, and subsequent deprotection of the protecting group(s).

Example 18

The reaction was carried out as described in Example 3 using a mixture of minor components ($C_{2a}$, $D_1$, $D_2$ and E) of antibiotic GE 2270 starting material instead of factor $A_3$ and methyl 6-aminocaproate hydrochloride (Fluka). $R_t$ (min) refer to HPLC method M reported in the HPLC analysis section.

When Y=—NH $CH_2CH_2CH_2CH_2CH_2COOCH_3$, $R_t$ (min) are respectively 43.43 for GE 2270 factor $C_{2a}$, 39.42 for GE 2270 factor $D_1$, 42.29 for GE 2270 factor $D_2$ and 37.41 for GE 2270 factor E.

When Y=—NH $CH_2CH_2CH_2CH_2CH_2COOH$, $R_t$ (min) are respectively 17.23 for GE 2270 factor $C_{2a}$, 15.76 for GE 2270 factor $D_1$, 16.64 for GE 2270 factor $D_2$ and 15.13 for GE 2270 factor E.

PROCEDURE M—Reaction of a selected mixture of minor components ($C_{2a}$, $D_1$, $D_2$ and E) of antibiotic GE 2270 starting material with the selected amine containing unprotected acid moieties.

Example 19

The reaction was carried out as described in Example 5 using a selected mixture of minor components ($C_{2a}$, $D_1$, $D_2$ and E) of antibiotic GE 2270 starting material instead of factor $A_3$ and 6-aminocaproic acid. (Fluka).

$R_t$ (rain) refer to Method M reported in the HPLC analysis section and are respectively 17.23 for GE 2270 factor $C_{2a}$, 15.76 for GE 2270 factor $D_1$, 16.64 for GE 2270 factor $D_2$ and 15.13 for GE 2270 factor E.

PREPARATION OF THE STARTING MATERIALS

1. The following starting materials have been purchased from Fluka (Fluka, Chemika-Biochemika, Buchs, Switzerland):

Glycine ethyl ester hydrochloride,
L-threonine methyl ester hydrochloride,
L-tyrosine methyl ester hydrochloride,
L-leucine methyl ester hydrochloride,
L-phenylalanine methyl ester hydrochloride,
L-methionine methyl ester hydrochloride,
L-proline methyl ester hydrochloride,
L-threonine methyl ester hydrochloride,
Nα-Cbz-L-lysine,
methyl 4-aminobutyrate hydrochloride,
methyl 6-aminocaproate hydrochloride,
6-aminocaproic acid,
4-(methylamino)benzoic acid,
piperidine-4-carboxylic acid,
N-methyl-D-glucamine,
D(+)-glucosamine hydrochloride,
2-dimethylaminoethylamine,
amino acetaldehyde dimethylacetal,
β-alanine ethyl ester hydrochloride.

The following starting materials have been purchased from Sigma (Sigma, Biochemicals:

2. Organic Compounds, St. Louis, U.S.A.):
Nδ-Cbz-L-ornithine,
L-aspartic acid dimethyl ester hydrochloride.

3. The following starting materials have been purchased from Aldrich (Aldrich, Catalogo Prodotti di Chimica Fine, Milano, Italy):

L-Prolinamide,
taurine,
3-amino-1-propanesulfonic acid,
3-aminopropylphosphonic acid,
4-amino-1-benzylpiperidine.

Production of antibiotic GE 2270 for preparing antibiotic GE 2270 factors A, $B_1$, $B_2$, $C_1$, $C_2$, $C_{2a}$, $D_1$, $D_2$, and E A culture of *Planobispora rosea* ATCC 53773 is grown on an oatmeal agar slant for two weeks at 28°–30° C. and then used to inoculate 500 ml flasks containing 100 ml of a seed media of the following composition:

Starch 20 g/l
Polypeptone 5 g/l
Yeast extract 3 g/l
Beef extract 2 g/l
Soybean meal 2 g/l
Calcium carbonate 1 g/l
Distilled water q.s. 100 ml (adjusted to pg 7.0 before sterilization)

The flask is incubated on a rotary shaker (200 rpm) at 28°–30° C. for 92 h. The obtained culture is then used to inoculate a jar fermenter containing 4 liters of the same medium and the culture is incubated at 28°–30° C. for 48 hours with stirring (about 900 rpm) and aeration (about one standard liter of air per volume per minute).

The obtained broth is transferred to a fermenter containing 50 l of the following production medium:

Starch 20 g/l
Peptone 2.5 g/l
Hydrolyzed casein 2.5 g/l
Yeast extract 3 g/l
Beef extract 2 g/l
Soybean meal 2 g/l
Calcium carbonate 1 g/l
Distilled water q.s. (adjusted to pH 7.0 before sterilization) and incubated for about 72 hours at 28°–30° C.

Antibiotic production is monitored by paper disc agar assay using *B. subtilis* ATCC 6633 grown on minimum Davis medium. The inhibition zones are evaluated after incubation overnight at 35° C.

4a) Recovery of crude antibiotic GE 2270

The fermentation mass (50 l) obtained above is harvested and submitted to filtration in the presence of a filter aid (Clarcell).

Antibiotic GE 2270 is found mainly in the mycelium, even if a certain amount of it can be recovered also from the filtrates.

The filtrate is adjusted to about pH 7.0 and extracted with ethyl acetate (50 l). The organic phase is separated by centrifugation and concentrated to a small volume under reduced pressure. The obtained oily residue is then treated with petroleum ether to precipitate crude antibiotic GE 2270 that is collected by filtration and dried. 415 mg of crude antibiotic GE 2270 complex is obtained.

The mycelium is extracted twice with 20 l of methanol and the pooled extracts are concentrated under reduced pressure to give an aqueous residue which is extracted twice with ethyl acetate. Crude antibiotic if GE 2270 (6.06 g) is precipitated by addition of petroleum ether from the concentrated organic phase.

4b) Isolation of antibiotic GE 2270 factor A

The crude obtained from the mycelium according to the procedure described above (3 g) is dissolved tetrahydrofuran and concentrated under reduced pressure in the presence of silica gel (230–400 mesh). The obtained solid residue is collected and applied to a chromatography column containing 300 g of silica gel (230–400 mesh) prepared in methylene chloride ($CH_2Cl_2$). The column is developed first with methylene chloride (2 l) and then sequentially with 1.5 l mixtures methylene chloride and methanol in the following ratios 98/2; 96/4, 94/6, 92/8, 90/10 and 88/12 (v/v).

Fractions are collected, analyzed by TLC, HPLC or microbiologically against *B. subtilis* and pooled according to their antibiotic content.

The pooled fractions containing antibiotic GE 2270 factor A are concentrated under reduced pressure to give an oily residue which is solubilized with tetrahydrofuran.

From this solution, antibiotic GE 2270 factor A (600 mg) is precipitated by adding petroleum ether.

4 bis) isolation of mixtures of minor components of a antibiotic GE 2270

A representative mixture particularly enriched in the minor components $C_{2a}$, $D_1$, $D_2$ and E was established by HPLC comparison with analytical samples of each single component.

$R_t$ (min) refer to HPLC method M reported in the HPLC analysis section and are 20.55 for GE 2270 factor $C_{2a}$, 17.43 for GE 2270 factor $D_1$, 18.17 for GE 2279 factor $D_2$, and 16.61 for GE 2270 factor E.

Concentration of this fraction under reduced pressure produced an oily residue which was redissolved in tetrahydrofuran and precipitated with petroleum ether as whitish powder.

4c) Separation and isolation of antibiotic GE 2270 factors $B_1$, $B_2$, $C_1$, $C_2$, $D_1$, $D_2$, and E Antibiotic GE 2270 factors $D_1$, $D_2$ and E are separated and purified from the above obtained crude mixture by preparative HPLC using a 250×20 mm column packed with Nucleosil® C18 (silica gel functionalized with octadecylsilane groups) (5 µm) and eluted with mixtures of Phase A: $CH_3CN$: tetrahydrofuran: 40 mM $HCOONH_4$ (40:40:20); Phase B: $CH_3CN$:tetrahydrofuran:40 mM $HCOONH_4$ (10:10:80). The antibiotic mixture (6 mg) was solubilized in 3 ml of Phase B and 1 ml of Phase A and was injected into the HPLC column which was eluted flow rate of 14 ml/min with a 26:74 mixture of Phase A and B. The eluted fractions were collected according to the UV adsorption profile at 254 nm. The fractions of subsequent chromatographic runs having homogeneous content were pooled and concentrated under reduced pressure to eliminate $CH_3CN$. The residual solution showed antibacterial activity against *Staphylococcus aureus* Tour L165 by paper disc assay. These solutions were lyophilized at least three times to remove completely the $HCOONH_4$ buffer residue from the HPLC phases.

The yields were as follows: antibiotic GE 2270 factor E, 11 mg; antibiotic GE 2270 factor $D_1$, 12 mg; antibiotic GE 2270 factor $D_2$, 10 mg.

4d) Isolation of a purified mixture containing antibiotic GE 2270 factor $C_{2a}$ in mixture with other GE 2270 factors The preparations of crude GE 2270 factors from 6 repeated fermentations were pooled and solubilized; into 12 l of $CH_2Cl_2$: methanol (93:7). The insoluble material was removed by filtration and the solution, containing the antibiotic complex, was applied to a 13 kg (230–400 mesh) silica gel column equilibrated in $CH_2Cl_2$:methanol (93:7). Antibiotic GE 2270 factor $C_{2a}$ was eluted from the column by eluting with $CH_2Cl_2$: methanol (93:7). The fractions containing the antibiotic of the invention (HPLC analysis) were pooled, were concentrated under reduced pressure and were dried to yield 23.5 g of antibiotic GE 2270 factor $C_{2a}$ in mixture with other minor factors.

A portion (5.5 g) of this preparation was again purified by flash chromatography on a column containing 400 g of silica gel (230–400 mesh) equilibrated in methylene chloride ($CH_2Cl_2$). The column was developed first with methylene chloride (1 liter) and then sequentially with a series of mixtures of methylene chloride/methanol in the following ratios (v/v): 96/4 (3 liters); 94/6 (1 liter); 92/8 (2 liters); 90/10 (6 liters) and 88/12 (4 liters).

The fractions containing mainly GE 2270 factor $C_{2a}$ (HPLC analysis) were pooled and were concentrated The antibiotic preparation (646 mg) was precipitated upon addition of petroleum ether.

4e) Isolation of pure antibiotic GE 2270 factor $C_{2a}$

The purified mixture containing mainly antibiotic GE 2270 factor $C_{2a}$ was further purified by preparative HPLC from the above described preparation.

A portion of the above described preparation for the antibiotic (10 mg) was solubilized in 1 ml of Phase A ($CH_3CN$: tetrahydrofuran: 40 mM $HCOONH_4$—40:40:20) and 1 ml of Phase B ($CH_3CN$: tetrahydrofuran: 40 mM $HCOONH_4$—10:10:80) and was injected into a HPLC 250× 20 mm Hibar column (E. Merck; Darmstadt F. R. Germany) pecked with 7 µm Nucleosil °C18 (silica gel functionalized with octadecylsilane groups) which was equilibrated with a mixture of 40% Phase A and 60% Phase B. The column was eluted at 15 ml/min flow rate with 22 minutes linear gradient from 40% to 50% of Phase A. The UV detection was 254 nm. The fractions of 10 subsequent chromatographic runs containing the pure antibiotic of the invention were pooled and were concentrated under reduced pressure to eliminate $CH_3CN$. Antibiotic GE 2270 factor $C_{2a}$ precipitated from water. The precipitate was collected by centrifugation, was washed twice with distilled water and was dried under vacuum yielding 66 mg of the pure antibiotic.

Preparation of antibiotic GE 2270 factor $A_2$

Antibiotic GE 2270 factor A (prepared as described above) (86 mg) is dissolved in 17 ml of 95% ethanol and 1.7 ml of acetic acid. After incubation at 60° C. for 24 h, the resulting solution is diluted with 0.1M sodium phosphate buffer pH 7.5 (100 ml) and adjusted to pH 7.5 with 1M sodium hydroxide. Ethanol is removed by evaporation under reduced pressure and the aqueous residue is extracted twice with ethyl acetate (100 ml). The organic phase is concentrated under reduced pressure to obtain a solid residue which is solubilized with tetrahydrofuran and then precipitated by adding petroleum ether. Antibiotic GE 2270 factor $A_2$ (62 mg) is obtained with minor amounts of antibiotic GE 2270 factors A and $A_1$. Pure antibiotic GE 2270 factor $A_2$ is obtained by preparative HPLC as follows:

10 Mg of the above crude product is solubilized in tetrahydrofuran, diluted to the solubility limit With water and then injected into a HPLC system with a column (250×20 mm) packed with Nucleosil® C18 (5 micrometer) reverse phase silica gel by Stacroma®, eluting with a linear gradient from 64% to 93% of phase B in phase A, in 20 min, at a flow rate of about 15 ml/min. In this system, phase A is a 90:10 (v/v) mixture of 18 mM sodium phosphate pH 7.2 and acetonitrile, while phase B is a 40:60 (v/v) mixture of 18 mM sodium phosphate pH 7.2 and acetonitrile. Fractions of five consecutive runs are collected and UV monitored at 330 nm. Fractions which contain substantial amounts of antibiotic GE 2270 factor $A_2$, which correspond to the major peaks of the UV elution profile, are pooled and concentrated under reduced pressure to an aqueous phase which is extracted twice with ethyl acetate. This organic layer is then washed with distilled water to remove the residual inorganic salts and concentrated to precipitate a Solid residue that is then dissolved in tetrahydrofuran and re-precipitated with petroleum ether, to obtain pure antibiotic GE 2270 factor $A_2$ (45 mg).

In European Patent Application Publication No. 406745 are described other alternative method preparing antibiotic GE 2270 factor $A_2$ as main reaction product of antibiotic GE 2270 factor A.

6. Preparation of antibiotic GE 2270 factor $A_3$

Antibiotic GE 2270 factor $A_2$ is incubated for 1 h at room temperature in 0.5M sodium carbonate. The reaction mixture is then diluted with cold water and brought to pH 6.5 with hydrochloric acid. The neutralized solution contains antibiotic GE 2270 factor $A_3$ as the main reaction product. This antibiotic is extracted from the aqueous phase with ethyl acetate and then is precipitated from the concentrated organic phase by adding petroleum ether.

Pure antibiotic GE 2270 factor $A_3$ is obtained by column chromatography as described below:

1.5 Grams of crude GE 2270 $A_3$ is dissolved in 60 ml of a 1/1 (v/v) mixture of methanol and dichloromethane and adsorbed on silica gel (75–230 mesh) by evaporation of the solvents under reduced pressure. The solid residue is then put on the top of a silica gel (75–230 mesh) column (bed height 40 cm) equilibrated with dichloromethane. The column is then eluted with mixtures of methanol in dichloromethane in the order: 1) 2% methanol (450 ml); 2) 5% methanol (500 ml); 3) 10% methanol (600 ml); 4) 15% methanol (500 ml); 5) 20% methanol (500 ml); 6) 30% methanol (250 ml).

Fractions are collected and monitored by TLC and a microbiological assay on *B. subtilis* ATCC 6633. Antibiotic GE 2270 factor $A_3$ is normally present in the eluates which contain about 15–20% methanol.

The fractions containing the desired product are pooled and concentrated under reduced pressure. Upon addition of petroleum ether to the residue, antibiotic GE 2270 factor $A_3$ precipitates (854 mg of pure product).

7. Preparation of the proper starting material from antibiotic factors $D_1$, $D_2$, E and $C_{2a}$ By substantially following the same procedure described at points 5 and 6 above but starting from the single factors $D_1$, $D_2$, E and $C_{2a}$ of antibiotic GE 2270 instead of factor A, the proper starting materials of formula III wherein W is COOH or an activated ester, R is hydrogen or $CH_2OH$, $R_1$ is $CH_3$ or hydrogen and $R_4$ is hydroxymethyl or methyl, are obtained.

7a) Preparation of proper starting material from a mixture of minor components ($C_{2a}$, $D_1$, $D_2$ and E) of antibiotic GE 2270

By substantially following the same procedure described at point 5 and 6 above but starting from a mixture of minor components ($C_{2a}$, $D_1$, $D_2$ and E) of antibiotic GE 2270 instead of the single factor A, the proper starting material of formula III wherein W is COOH or an activated ester and R, $R_1$ and $R_4$ are respectively methoxymethyl, methyl and hydroxymethyl for $C_{2a}$, hydrogen, hydrogen and methyl for $D_1$, hydroxymethyl, methyl and methyl for $D_2$ and hydroxymethyl, hydrogen and methyl for E are obtained.

$R_t$ (min) refer to HPLC method M reported in the HPLC analysis section.

When W is an activated ester, $R_t$ (min) are respectively 22.51 for GE 2270 factor $C_{2a}$, 19.80 for GE 2270 factor $D_1$, 20.41 for GE 2270 factor $D_2$ and 18.92 for GE 2270 factor E.

When W is COOH, $R_t$ (min) are respectively 12.99 for GE 2270 factor $C_{2a}$, 10.38 for GE 2270 factor $D_1$, 11.08 for GE 2270 factor $D_2$ and 9.03 for GE 2270 factor E.

8. Preparation of glycyl-N∈-Cbz-L-lysine trifluoroacetate 4.8 ml of DPPA (22 mmols) was added at 0° C. to a well stirred solution of 3.5 g of BOC-glycine (Fluka): (20 mmols) and 7.28 g of N∈-Cbz-L-lysine methyl ester hydrochloride (Fluka) (22 mmols) in 50 ml of dry DMF. To this solution, a solution of 5.8 ml of TEA (42 mmols) in 50 ml of dry DMF was added at 0° C. over a 10–15 min period. Stirring was continued for 2 more hours at 0° C. and then overnight at room temperature. The reaction mixture was diluted with 250 ml of toluene and 500 ml of ethyl acetate and washed with 1N aq. HCl (×3), water, a saturated solution of $NaHCO_3$ and brine. Drying over $Na_2SO_4$ and evaporation of the solvent yielded 9.7 g of a thick oil which resisted any attempt of crystallization. NMR of this oil was in perfect agreement with the structure of BOC-glycyl-N ∈Cbz-L-lysine methyl ester.

The oil was dissolved in 200 ml of acetone/dioxane 1:1 and 22 ml of 1N aq. NaOH were added over a 30 min period at 0°C. under stirring. The reaction was then stirred for 45 min at room temperature, diluted with 300 ml of cold water, acidified with 25 ml of 1N aq HCl and extracted with chloroform (×3) and ethyl acetate (×3). Drying over $Na_2SO_4$ and evaporation of the solvent yielded 9.4 g of a gum which resisted any attempt of crystallization. NMR of this gum was in perfect agreement with the structure of BOC-glycyl-N ∈-Cbz-L-lysine.

The gummy compound was treated with 20 ml of cold trifluoroacetic acid (TFA). The reaction mixture was swirled at room temperature until all the compound went in solution. The solution was reduced to a small volume under vacuum in the cold and then ethyl ether was added to induce precipitation of the title compound. 9.6 g of glycyl-N ∈-Cbz-L-lysine trifluoroacetate were obtained as a white powder. NMR was in perfect agreement with the structure. Preparation of L-tyrosyl-L-prolinamide.

0.48 ml of DPPA (2 mmols) were added at 0° C. to a well stirred solution of 538 mg of BOC-L-tyrosine (Fluka) (2 mmols), 228.3 mg of L-prolinamide (Aldrich) (2 mmols) and 168 mg of $NaHCO_3$ in 5 ml of dry DIFF. The reaction was stirred for 24 h at room temperature and then diluted with 50 ml of water and extracted with chloroform (×3). The organic phase was washed water, dried over $Na_2SO_4$ and the solvent evaporated to yield an oil which was purified by flash chromatography on silica gel 60 (230–400 mesh ASTM-Merck) eluting with hexane/acetone 2:3. 420 mg of BOC-L-tyrosyl-L-prolinamide were in this way obtained as a white solid. NMR was in agreement with the structure.

The solid obtained was dissolved in 6 ml of ethyl acetate and stirred for 48 h at room temperature in the presence of 4 ml of 3N aq. HCl The reaction mixture was then evaporated to dryness in vacuo and the residue redissolved in ethanol was precipitated with ethyl ether. 302 mg of L-tyrosyl-L-prolinamide were obtained as a white powder. NMR was in perfect agreement with the structure.

10. Preparation of methyl 8-aminocaprylate and methyl 11-aminoundecanoate p-toluenesulfonates A solution of 40 mmols of the selected amino acid (Fluka) and 15.2 g of p-toluenesulfonic acid monohydrate (Fluka) (80 mmols) in 200 ml of methanol was refluxed overnight. The solvent was then evaporated in vacuo and the residue redissolved in ethyl ether. After sometime the title compounds crystallized out quantitatively. The NMR of both compounds was in agreement with their structure.

11. Preparation of 5-aminopentylphosphonic acid 3.48 g of 5-amino-1-pentanol (Fluka) (33.7 mmols) and 5.0 g of phthalic anhydride (Fluka) (33.7 mmols) were melted together at 180° C. This temperature was maintained for 90 min until no more water developed. The reaction was allowed to cool to room temperature and the oily mixture was chromatographed on silica gel 60 (230–400 mesh ASTM-Merck) eluting with 2% methanol in chloroform. 5.9 g of a pure oil were obtained. NMR was in agreement with the structure.

To the 5.9 g of the oily intermediate (25 mmols), 1.6 ml of $PBr_3$ (17 mmols) were added portionwise so to control the exothermic reaction. The reaction mixture was heated at 100° C. for 1.5 h and then poured into crushed ice. The solid material that separated was filtered and allowed to dry in air overnight. 6.6 g of the pure bromo intermediate were obtained. The mass was in agreement with the expected molecular weight.

500 mg of the pure bromo intermediate (1.69 mmols) and 140 mg of triethyl phosphite (Fluka) (0.84 mmols) were heated together at 150° C. for about 1 h. Other three portions of 140 mg of triethyl phosphite were then added at 30 min interval at the same temperature. When all the starting material had disappeared, the excess of triethyl phosphite was distilled off and the crude material purified by flash chromatography on silica gel 60 (230–400 mesh ASTM-Merck) eluting with 2% methanol in dichloromethane. 468 mg of the expected diethyl phosphonate were obtained as a thick oil. NMR confirmed the structure.

468 mg of the diethyl phosphonate intermediate were treated overnight with 3 ml of a 0.2M solution of hydrazine in methanol at room temperature. The precipitated phthalhydrizide was filtered off and the remaining solution was evaporated to dryness in vacuo. The residue was taken up in 1N aq. HCl and the solution was washed with ethyl acetate, basified with NaOH and extracted several times with n-butanol. The butanolic phase was dried over $Na_2SO_4$ and evaporated to dryness to yield 175 mg of a thick oil whose NMR was in agreement with the product expected.

175 mg of diethyl 5-aminopentylphosphonate were refluxed for 20 h in 0.6 ml of conc. HCl. The acid solution was then evaporated to dryness by azeotropic distillation in vacuo in the presence of n-butanol. The NMR of the glassy oil obtained confirmed it to be the 5-aminopentylphosphonic acid.

12. Preparation of 5-(5-aminopentyl)tetrazole

To a solution of 10 ml of 6-aminocapronitrile (Fluka) (80 mmols) and 13.3 ml of TEA (96 mmols) in 80 ml of tetrahydrofuran, 12.48 ml of benzyl chloroformate (Fluka) (88 mmols) were added dropwise at 0° C. under stirring. Stirring was continued for 2 h at room temperature and the solvent was evaporated in vacuo. The residue was dissolved in ethyl acetate, washed with 1N aq. HCl, water and then dried over $Na_2SO_4$ and the solvent evaporated to yield 19.6 g of a syrup whose NMR was in agreement with the structure.

1 g of the protected 6-aminocapronitrile (4.06 mmols) in 40 ml of 1-methyl-2-pyrrolidone was heated at 150° C. under argon in the presence of 793 mg of sodium azide (12.2 mmols) and 834 mg triethylamine hydrochloride (6.1 mmols). After 4 h the reaction mixture was diluted with 120 ml of water and then carefully acidified to pH 1 with 10% aq. HCl (attention: azotidric acid forms!). The solution was extracted with ethyl acetate, the organic phase re-extracted with 10% aq. NaOH (×2) and the basic solution washed with ethyl ether, acidified with conc. HCl and extracted with ethyl acetate (×3). Drying and evaporation of the organic phase yielded a syrup that crystallized from methanol/water. 260 mg of a fine powder were obtained. NMR and mass confirmed the structure.

250 mg of the N-protected amino tetrazole (0.86 mmols) were treated at room temperature with 5 ml of thioanisole (43.25 mmols) and 17.5 ml of trifluoroacetic acid for 3 h. Trifluoroacetic acid was concentrated in vacuo in the cold and ethyl ether was added to precipitate the title compound as its trifluoroacetate salt. NMR and mass confirmed the structure.

13. Preparation of N-[3,4-di-(O-tetrahydropyranyl)benzoyl]-thiazolidin-2-thione

A solution of 4.62 g of 3.4-dihydroxybenzoic acid (Fluka) (30 mmols) in 40 ml of methanol was refluxed for 24 h in the presence of 0.325 ml of conc. $H_2SO_4$. After cooling the solution to room temperature some solid $NaHCO_3$ was added and the solvent evaporated in vacuo. The residue was taken up in ethyl acetate, washed with water, dried over $Na_2SO_4$ and the solvent evaporated to yield a syrup which was crystallized from ethyl acetate/hexane. 3.53 g of white crystals were obtained.

9.1 ml of dihydropyrane (Fluka) (0.1 mol) and 250 mg of pyridinium p-toluenesulfonate (1 mmol) were added at room temperature to a stirred solution of 1.68 g of methyl 3,4-dihydroxybenzoate (10 mmols) in 4 ml of ethyl acetate and 25 ml of dichloromethane. After 4 d the reaction mixture was washed with a saturated solution of $NaHCO_3$, dried over $Na_2SO_4$ and evaporated to dryness to obtain 3.36 g of an oil which was used for the next step without further purification.

The crude from the previous reaction was dissolved in 40 ml of acetone and to the stirred solution 20 ml of water, 2.76 g of $K_2CO_3$ (20 mmols) and 10 ml of 1N aq. NaOH (10 mmols) were added and stirring was continued for 7 d at room temperature. Acetone was evaporated in vacuo and the residual water phase was washed with ethyl acetate. The aqueous phase was transferred to an E. flask containing an equal volume of chloroform, cooled to 0° C. and carefully acidified under vigorous stirring with 50 ml of 1N aq. HCl. The water phase was then extracted 3 more times with chloroform and the combined organic layers were washed with 0.2% ammonium formate, dried over $Na_2SO_4$ and evaporated to dryness to yield a syrup which crystallized after hexane addition. 2.34 9 of a white solid were obtained. The NMR was in agreement with the structure.

333 mg of 2-thiazoline-2-thiol (Fluka) (2.8 mmols), 577 mg of N,N'-dicyclohexylcarbodiimide (Fluka) (2.8 mmols) and 35 mg of 4-dimethylamino-pyridine were added in the order at 0° C. to a stirred solution of 644 mg of the benzoic acid intermediate (2 mmols) in 14 ml ethyl acetate/dichloromethane 5:2. Stirring was continued overnight at room temperature, the precipitated dicyclohexylurea was filtered off and the yellow solution was evaporated in vacuo to yield yellow oil which was purified by flash chromatography on silica gel 60 (230–400 mesh ASTM-Merck) eluting from 25% acetone in hexane. 708 mg of yellow crystals were obtained from acetone/hexane. NMR and IR confirmed the compound to be the title compound.

14. Preparation of $N^1$-$N^8$-di-tert-butoxycarbonylspermidine

A solution of 19.72 g of BOC-ON (Aldrich) (80 mmols) in 60 ml of degassed tetrahydrofuran (THF) was added dropwise over a 1 h period under argon to a stirred solution of 5.8 g of spermidine (Aldrich) (40 mmols) in 40 ml of degassed THF cooled at 0° C. The reaction was then stirred at room temperature overnight and then evaporated to dryness. The residue was taken up in ethyl ether, washed with 1N aq. NaOH (×4) and water (×4), dried over $Na_2SO_4$ and the solvent concentrated to a small volume in vacuo. Upon addition of ethyl ether 11 g of a white powder precipitated. NMR confirmed it to be the title compound.

15. Preparation of N-tert-butoxycarbonylpropilendiamine 4.2 g of BOC-ON (Aldrich) (17.2 mmols) were added at room temperature to a stirred solution of 2 g of 3-aminopropionitrile fumarate (Aldrich) (15.6 mmols) dissolved in a mixture of 10 ml of dioxane, 10 ml of water and 3.3 ml of triethylamine. After 3 h the reaction mixture was diluted with more water and extracted with dichloromethane (×3). The combined organic layers were washed with 1N aq. NaOH (×3) and water (×3), dried over $Na_2SO_4$ and evaporated to dryness. The residual oil was taken up in ethyl ether and precipitated with hexane to yield 2.2 g of a white powder.

1 g of N-BOC-protected intermediate (5.9 mmols) in 7 ml of 1N ethanolic NaOH was hydrogenated at 40 psi in the presence of 130 mg of Raney nickel (50% slurry in water, pH>9) (Aldrich) for 40 h. Raney nickel was filtered off and the solvent was evaporated to dryness. The residue was taken up in ethyl acetate and washed with 1 N aq. NaOH, dried over $Na_2SO_4$ and the solvent removed in vacuo yielding 950 mg of a colorless oil which solidified on standing. NMR confirmed it to be the title compound.

16. Preparation of 3-(2-aminoethylthio)propanoic acid methyl ester trifluoroacetate To a solution of 0.5 g of cysteamine (Fluka) (6.48 mmols) in 5 ml of $CH_2Cl_2$, 1.4 g of di-tert-butyl dicarbonate (Aldrich) (6.48 mmols) in 5 ml of $CH_2Cl_2$ were added at room temperature under stirring. After 30 min the organic solvent was evaporated and the crude material dissolved in 5 ml of absolute ethanol. To the ethanolic solution, 2.7 ml of TEA (19.1 mmols) and 1.07 ml of methyl 3-bromopropionate (Fluka) (9.57 mmols) were added in the order. The reaction was completed in about 30 min. Ethanol was removed in vacuo and replaced by 15 ml of chloroform. The organic phase was then washed with water, anidrified on $Na_2SO_4$ and solvent evaporated to yield an oil which was finally treated with 1 ml of trifluoroacetic acid at 0° C. for 5 min. Evaporation to dryness gave 270 mg of a pale yellow oil. NMR and IR confirmed it to be the title compound 17. Preparation of 6-amino-2(E)-hexenoic acid To a stirred solution of 2 ml of 4-amino-butyraldehyde diethyl acetal (Fluka) (11.6 mmols) and 3.6 ml of TEA (25.6 mmols) in 5 ml of $CH_2Cl_2$, a solution of 1.5 ml of benzoyl chloride (Fluka) (12.9 mmols) in 5 ml $CH_2Cl_2$, was added in 30 min. at room temperature. After 1 hour the reaction was diluted with 10 more ml of $CH_2Cl_2$, washed with water and the organic phase dried over $Na_2SO_4$ and the volume adjusted to 20 ml. The new solution was allowed to react for three days under argon in the presence of 1.6 ml of TEA (11.5 mmols), 10.2 g of di-tert-butyl dicarbonate (Aldrich) (46.8 mmols) and 1.4 g of 4-dimethylamino-pyridine (Fluka) (11.5 mmols) at room temperature. Removal of the solvent gave a brown oil that was purified by flash chromatography on silica gel 60 (230–400 mesh ASTM-Merck) eluting with 20% ethyl acetate in n-hexane yielding 1.6 g of the N,N deprotected 4-aminobutyraldehyde diethyl acetal as a colorless oil. NMR confirmed the structure.

The obtained oil was then dissolved in 5 ml of THF and treated with 5 ml of 1N HCl at room temperature for three hours. THF was removed in vacuo and the remaining solution was washed with chloroform (2 ml×3). The organic phase was then washed with a solution of $Na_2CO_3$, water, dried over $Na_2SO_4$ and evaporated to dryness yielding an oil that was used in the next step without further purification.

To a suspension of 160 mg of 60% NaH (4 mmols) in 5 ml of dry THF at 0° C. under argon, 0.837 ml of triethylphosphonoacetate (Fluka) (4.3 mmols) were added. After 30 min. a dry THF (2 ml) solution of the previously obtained aldehyde (1.17 g) (4.02 mmols) was added and the temperature was allowed to rise to room temperature. The reaction was stirred overnight and then 50 more mg of 60% NaH were added at 0 C. After two more hours at room temperature the reaction mixture was treated with diluted HCl (10 ml) and extracted with ethyl acetate (5 ml×3). The combined organic phase was washed with water, dried over $Na_2SO_4$ and evaporated to dryness. The crude material was purified by flash chromatography on silica gel 60 (230–400 mesh ASTM-Merck) eluting with 15% ethyl acetate in n-hexane yielding 765 mg of a syrup. NMR confirmed it to be the expected product with the double bond in E configuration (J=16 Hz).

6.15 ml of 1N LiOH (6.15 mmols) were added to a solution of 739 mg of the unsaturated ester previously obtained (2.05 mmols) in 10 ml of THF under stirring at room temperature. When the starting material had disappeared the reaction mixture was concentrated in vacuo at 30° C. (bath temperature). The aqueous solution was acidified at pH 2 with 1N HCl and then extracted with ethyl acetate. The combined organic phase was dried over $Na_2SO_4$, filtered and the solvent evaporated yielding an oil that solidified upon standing under vacuum. NMR and MS confirmed it to be 6-N-BOC-amino-2(E)-hexenoic acid.

Removal of the N-BOC protection to obtain the title compound was carried out in neat trifluoroacetic acid at 0°C. just before the coupling with the appropriate GE 2270 starting material.

18. Preparation of 3-(2-aminoethoxy)propanoic acid trifluoroacetate

To a stirred solution of 1 g of N-BOC-ethanolamine (6.22 mmols) [prepared according to classical methodologies from ethanolamine (Fluka)] in 10 ml of dry THF at –78 C., 3.88 ml of 1.6M solution of butyllithium (Fluka) (6.22 mmols) were added under argon. After 30 min. 1.3 g of t-butyl 3-bromo propanoate [prepared according to classical methodologies from 3-bromo propanoic acid (Fluka)] (6.22 mmols) were added, the temperature allowed to rise to room temperature and the resulting mixture stirred for 20 hours at that temperature. After dilution with water the reaction mixture was extracted with n-hexane (5 ml×2). Removal of the solvent gave a crude material that was purified by flash chromatography on silica gel 60 (230–400 mesh ASTM-Merck) eluting with 20% ethyl acetate in n-hexane yielding 1.43 g of an oil. NMR confirmed it to be the coupled compound.

The total deprotection of the coupled compound was carried out immediately before addition to the appropriate GE 2270 starting material by stirring it in trifluoroacetic acid for about 5 min at room temperature. Removal of trifluoroacetic acid in vacuo yielded the title compound.

We claim:

1. An amide derivative of antibiotic GE 2270 having the following formula I

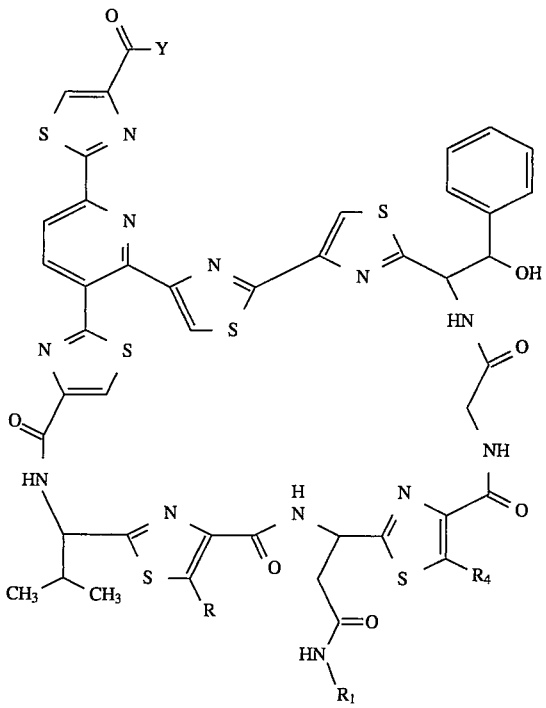

wherein

R represents:
hydrogen, hydroxymethyl, or methoxymethyl;

$R_1$ represents:
hydrogen, or methyl;

Y represents:
a group of formula

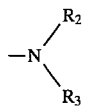

wherein:

$R_2$ represents:
hydrogen, $(C_1-C_4)$alkyl, amino$(C_2-C_4)$alkyl, $(C_1-C_4)$alkylamino-$(C_1-C_4)$alkyl, or di-$(C_1-C_4)$alkylamino-$(C_1-C_4)$alkyl;

$R_3$ represents:
hydrogen; a linear or branched $(C_1-C_{14})$alkyl group bearing from 1 to 3 substituents selected from: carboxy, sulfo, phosphino, amino which may be optionally protected with a lower alkoxycarbonyl or a benzyloxycarbonyl group, $(C_1-C_4)$alkylamino wherein the alkyl moiety may be optionally substituted with a carboxy group, di-$(C_1-C_4)$alkylamino, hydroxy, halo, $(C_1-C_4)$alkoxy wherein the alkyl moiety may be optionally substituted with a carboxy group, $(C_1-C_4)$alkoxycarbonyl, mercapto, $(C_1-C_4)$alkylthio wherein the alkyl moiety may be optionally substituted with a carboxy group, phenyl which may be optionally substituted with 1 to 3 substituents selected from carboxy, sulfo, hydroxy, halo and mercapto, carbamyl, $(C_1-C_6)$alkylcarbamyl wherein the alkyl moiety may be optionally substituted with 1 or 2 substituents selected from carboxy, amino, $(C_1-C_4)$alkylamino and di-$(C_1-C_4)$alkylamino, di-$(C_1-C_4)$alkylcarbamyl wherein the alkyl moieties together with the adjacent nitrogen atom may also represent a saturated 5-7 membered heterocyclic ring which may optionally be substituted with a carboxy or a carbamyl group on one of the ring carbons and may optionally contain a further heterogroup selected from O, S and N, benzoylamino wherein the phenyl group may be substituted from 1 to 3 hydroxy group, a nitrogen containing 5-6 membered heterocyclic ring which may unsaturated, partially saturated or wholly saturated and may contain 1 to 3 further heteroatoms selected from N, S and O wherein one of the carbons of the ring may optionally bear a group carboxy, sulfo carboxy$(C_1-C_4)$alkyl or sulfo$(C_1-C_4)$alkyl and the ring nitrogen atom may optionally be substituted by $(C_1-C_4)$alkyl, carboxy$(C_1-C_4)$alkyl, sulfo$(C_1-C_4)$alkyl, or benzyl;

$(C_3-C_6)$alkenyl, optionally substituted by carboxy or sulfo;

1-deoxy-1-glucityl;

2-deoxy-2-glucosyl;

a fully saturated 5 to 7 membered nitrogen containing heterocyclic ring wherein the nitrogen atom may be optionally substituted by $(C_1-C_4)$alkyl or benzyl and one or two carbons of the ring skeleton may bear a substituent selected from $(C_1-C_4)$alkyl, carboxy and sulfo;

or $R_2$ and $R_3$ taken together with the adjacent nitrogen atom represent a fully saturated 5-7 membered heterocyclic ring which may optionally contain a further heteroatom selected from O, S and N, and may optionally bear one or two substituents on the ring carbons selected from $(C_1-C_4)$alkyl, benzyl, carboxy, sulfo, carboxy$(C_1-C_4)$alkyl, and sulfo$(C_1-C_4)$alkyl;

$R_4$ represents:
hydrogen, methyl, or hydroxymethyl;

with the proviso that when $R_4$ is hydrogen or hydroxymethyl, then simultaneously R is methoxymethyl and $R_1$ is methyl;

and the pharmaceutically acceptable addition salts thereof.

2. A compound according to claim 1 wherein R represents methoxymethyl and the other substituents are defined as in claim 1.

3. A compound as claimed in claim 1 wherein R represents methoxymethyl, $R_1$ and $R_4$ represent methyl and Y represents a group of formula

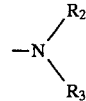

wherein $R_2$ is hydrogen and $R_3$ is defined as in claim 1.

4. A compound as claimed in claim 1 wherein R is methoxymethyl, $R_1$ and $R_4$ represent a methyl group and Y is an amino moiety which is derived from a natural amino acid selected from the group consisting of glycine, ornithine, serine, aspartic acid, tyrosine, leucine, phenylalanine, methionine, proline, threonine, and lysine, or a synthetic dipeptide selected from the group consisting of glycyllysine, serylproline, glycylprolinamide, tyrosylprolinamide, threonylprolinamide, and leucylprolinamide.

5. A compound as claimed in claim 1 wherein R is methoxymethyl, $R_1$ and $R_4$ are methyl, Y is a group $NR_2R_3$ wherein $R_2$ is hydrogen and $R_3$ is a linear alkyl chain of 3 to 12 carbons substituted with a group selected from COOH, $SO_3H$ and $PO_3H_2$.

6. A compound as claimed in claim 1 wherein R is methoxymethyl, $R_1$ and $R_4$ are methyl, Y is a group $NR_2R_3$ wherein $R_2$ is hydrogen and $R_3$ is $CH_2CH_2CH_2CH_2CH_2$—COOH.

7. A compound as claimed in claim 1 wherein R represents hydrogen, hydroxymethyl or methoxymethyl, $R_1$ represents hydrogen or methyl, $R_4$ represents hydrogen, methyl or hydroxymethyl and Y represents a group of formula

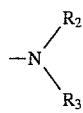

wherein $R_2$ is hydrogen and $R_3$ is defined as in claim 1.

8. A compound as claimed in claim 7 wherein Y is an amino moiety which is derived from a natural amino acid selected from the group consisting of glycine, ornithine, serine, aspartic acid, tyrosine, leucine, phenylalanine, methionine, proline, threonine, and lysine, or a synthetic dipeptide selected from the group consisting of glycyllysine, serylproline, glycylprolinamide, tyrosylprolinamide, threonylprolinamide, and leucylprolinamide.

9. A compound as claimed in claim 1 wherein R is hydrogen, hydroxymethyl or methoxymethyl, $R_1$ is hydrogen or methyl, $R_4$ is hydrogen, methyl or hydroxymethyl and Y is a group $NR_2R_3$ wherein $R_2$ is hydrogen and $R_3$ is a linear alkyl chain of 3 to 12 carbons substituted with a group selected from COOH, $SO_3H$ and $PO_3H_2$.

10. A compound as claimed in claim 1 wherein R is hydrogen, hydroxymethyl or methoxymethyl, $R_1$ is hydrogen or methyl, $R_4$ is hydrogen, methyl or hydroxymethyl and Y is a group $NR_2R_3$ wherein $R_2$ is hydrogen and $R_3$ is $CH_2CH_2CH_2CH_2CH_2$—COOH.

11. A compound according to claim 5 in which $R_3$ is represented by a linear alkyl chain of 3 to 7 carbons.

12. A compound according to claim 9 in which $R_3$ is represented by a linear alkyl chain of 3 to 7 carbons.

13. A pharmaceutical composition containing a compound of claim 1 as the active ingredient in admixture with a pharmaceutically acceptable carrier.

\* \* \* \* \*